United States Patent
Miller et al.

(10) Patent No.: US 10,126,242 B2
(45) Date of Patent: Nov. 13, 2018

(54) PURE SPECTRUM EXTRACTION FROM BIOLOGICAL SAMPLES IN FLUORESCENCE MULTISPECTRAL IMAGING

(71) Applicant: Caliper Life Sciences, Inc., Waltham, MA (US)

(72) Inventors: Peter J. Miller, Cambridge, MA (US); Kent S. Johnson, Cambridge, MA (US)

(73) Assignee: Caliper Life Sciences, Inc., Waltham, MA (US)

( * ) Notice: Subject to any disclaimer, the term of this patent is extended or adjusted under 35 U.S.C. 154(b) by 420 days.

(21) Appl. No.: 14/795,430

(22) Filed: Jul. 9, 2015

(65) Prior Publication Data

US 2016/0011116 A1 Jan. 14, 2016

Related U.S. Application Data

(60) Provisional application No. 62/022,635, filed on Jul. 9, 2014.

(51) Int. Cl.
*G01N 21/64* (2006.01)
*G01J 3/44* (2006.01)
*G01J 3/28* (2006.01)

(52) U.S. Cl.
CPC ............ *G01N 21/6486* (2013.01); *G01J 3/28* (2013.01); *G01J 3/2823* (2013.01); *G01J 3/4406* (2013.01); *G01N 21/6428* (2013.01); *G01N 21/6456* (2013.01); *G01N 2021/6419* (2013.01); *G01N 2021/6421* (2013.01); *G01N 2201/06113* (2013.01); *G01N 2201/12* (2013.01)

(58) Field of Classification Search
None
See application file for complete search history.

(56) References Cited

U.S. PATENT DOCUMENTS 8,551,786 B2 10/2013 Chan et al.
2013/0006117 A1 1/2013 Morishita

FOREIGN PATENT DOCUMENTS

CN 101809433 8/2010 ............ G01N 21/64
CN 102089646 6/2011 ............ G01N 21/64

OTHER PUBLICATIONS

Deliolanis, "In vivo tomographic imaging of red-shifted fluorescent proteins," Biomedical optics express, vol. 2(4), p. 887-900, 2011.*
ScienceDirect Topics, "Counterstain—an overview," 9 pages, 2013.*
Keshava, "Spectral unmixing," IEEE signal processing magazine, vol. 19(1), p. 44-57, 2002.*
International Preliminary Report on Patentability for International Application Serial No. PCT/US2015/039739 dated Jan. 19, 2017.
International Search Report and Written Opinion of the International Search Authority for International Application No. PCT/US2015/039739 dated Sep. 21, 2015 (13 pages).
Wamiq Manzoor Ahmed et al., "State of the Art in Information Extraction and Quantitative Analysis for Multimodality Biomolecular Imaging", *Proceedings of the IEEE*, vol. 96, No. 3, pp. 512-531.
Fei Liu et al., "Extraction of Target Fluorescence Signal from In Vivo Background Signal Using Image Subtraction Algorithm", *International Journal of Automation and Computing*, vol. 9, No. 3, pp. 232-236 (Jul. 7, 2012).
Zhengyu Pang et al., "Autofluorescence Removal Using a Customized Filter Set", *Microscopy Research and Technique*, vol. 76, pp. 1007-1015 (Jul. 16, 2013).
Stylianos Psycharakis et al., "Autofluorescence removal from fluorescence tomography data using multispectral imaging", *Proceedings of SPIE-OSA Biomedical Optics*, vol. 6626, pp. 662601-1-662601-7 (Jul. 5, 2007).
Chris H. A. Van de Lest et al., "Elimination of Autofluorescence in Immunofluorescence Microscopy with Digital Image Processing", *The Journal of Histrochemistry and Cytochemistry*, vol. 43, No. 7, pp. 727-730 (Jul. 1, 1995).
Chinese Office Action for Chinese Application No. 201580048121.6 dated Nov. 16, 2017 (21 pages).

* cited by examiner

Primary Examiner — G Steven Vanni
(74) Attorney, Agent, or Firm — Fish & Richardson P.C.

(57) ABSTRACT

The disclosure features methods that include obtaining multispectral image information for a sample that includes a fluorescent dye, calculating from an image cube of the information a first spectrum and a second spectrum, and calculating a pure spectrum of the fluorescent dye in the sample based on the first and second spectra, where a relative contribution of light emission from the fluorescent dye to the second spectrum is larger than a relative contribution of light emission from the fluorescent dye to the first spectrum, where calculating the first and second spectra includes identifying corresponding first and second sets of pixel intensity values in the image cube, and where identifying the first set of pixel intensity values includes designating one or more layers of the image cube as a first layer set.

30 Claims, 16 Drawing Sheets

PURE SPECTRUM EXTRACTION FROM BIOLOGICAL SAMPLES IN FLUORESCENCE MULTISPECTRAL IMAGING

CROSS-REFERENCE TO RELATED APPLICATIONS

This application claims priority to U.S. Provisional Patent Application No. 62/022,635, filed on Jul. 9, 2014, the entire contents of which are incorporated by reference herein.

TECHNICAL FIELD

This disclosure relates to imaging of biological samples, including systems and methods for determining pure spectra useful in analysis of fluorescent multiband or multispectral images.

BACKGROUND

Fluorescence imaging of biological cell and tissue samples is used to visualize the presence and expression levels of specific antigens, using probes that conjugate antibodies to fluorescent dyes. It is possible to visualize multiple proteins in a given tissue section using probes that target specific antigens of interest, together with one or more histological dyes such as DAPI, a nuclear counterstain. Other targets such as RNA or DNA can be visualized using fluorescent in situ hybridization and oligo-labeled fluorescent probes, respectively.

Fluorescence imaging of a dye involves exciting it with light of a first wavelength band or range of wavelengths, and observing light that it emits in response to this, in a second wavelength band or range of wavelengths. The propensity of a fluorescent dye to emit light in response to excitation at a given wavelength is termed its excitation spectrum. The wavelength distribution of the fluorescent light a dye emits is termed its emission spectrum.

When multiple dyes are used, they are typically chosen to have different excitation spectra, emission spectra, or both, so that by careful choice of the excitation wavelengths and emission wavelengths used, the dye that is being observed can be distinguished. When the spectra of the various fluorescent dyes are not distinct, but overlap substantially in terms of their excitation spectra and emission spectra, it becomes more difficult to determine what dye is associated with the observed emitted light that one observes.

Many samples exhibit endogenous fluorescence emission. That means that when optically excited, the sample itself emits fluorescent light, in addition to the fluorescent light emitted by fluorescent dyes used in connection with antibody-conjugated probes or as a counterstain. This can add further complexity to the above-mentioned determination.

Multispectral imaging of fluorescent samples involves acquiring a series of images of the sample at different excitation wavelengths, emission wavelengths, or combinations of the two. The various images are assembled into an image cube, where two dimensions of the cube correspond to spatial position in the sample, and the third dimension corresponds to the spectrum associated with the various excitation and/or emission wavelengths.

SUMMARY

In general, in a first aspect, the disclosure features methods that include: obtaining multispectral image information for a sample that includes a fluorescent dye, where the multispectral image information corresponds to an image cube comprising multiple two-dimensional layers, each layer corresponding to an image of the sample; calculating from the image cube a first spectrum that includes contributions from endogenous fluorescence in the sample; calculating from the image cube a second spectrum that includes contributions from the fluorescent dye and from endogenous fluorescence in the sample; and calculating a pure spectrum of the fluorescent dye in the sample based on the first and second spectra, where a relative contribution of light emission from the fluorescent dye to the second spectrum is larger than a relative contribution of light emission from the fluorescent dye to the first spectrum, where calculating the first and second spectra includes identifying corresponding first and second sets of pixel intensity values in the image cube and using the identified sets of pixel intensity values to calculate the first and second spectra; and where identifying the first set of pixel intensity values includes designating one or more layers of the image cube as a first layer set, and identifying members of the first set of pixel intensity values based on the first layer set.

Embodiments of the methods can include any one or more of the following features.

The first spectrum can include contributions from the fluorescent dye. Relative contributions from light emission by other components in the sample can be reduced (and even minimized) in the pure spectrum of the fluorescent dye relative to the second spectrum.

The methods can include, for each candidate pixel in the first layer set, determining whether the pixel is a member of the first set of pixel intensity values based on a fraction of total pixel intensity that is attributable to the first layer set. The methods can include designating one or more layers of the image cube as a second layer set, and identifying members of the second set of pixel intensity values based on the second layer set. The methods can include, for each candidate pixel in the first layer yet, determining whether the pixel is a member of the first set of pixel intensity values based on a fraction of total pixel intensity that is attributable to the first layer set. The methods can include, for each candidate pixel in the second layer set, determining whether the pixel is a member of the second set of pixel intensity values based on a fraction of total pixel intensity that is attributable to the second layer set. The methods can include identifying pixels that correspond to the sample based on the first set of layers.

The methods can include adding the pure spectrum of the fluorescent dye to a spectral library, obtaining a second set of multispectral image information for a second sample corresponding to a second image cube, where the second sample includes the fluorescent dye, and using the spectral library to unmix the second image cube to determine an amount of the fluorescent dye at multiple spatial locations in the second sample. The second sample can include a fluorescent counterstain, and the methods can include determining relative amounts of the fluorescent dye and the fluorescent counterstain at the multiple spatial locations in the second sample.

The methods can include determining the pure spectrum by subtracting from the second spectrum a scaled multiple of the first spectrum. The methods can include determining a value of a scaling coefficient that multiplies the first spectrum from pixel intensity values that correspond to multiple pixels in the image cube.

In another aspect, the disclosure features systems that include a radiation source configured to direct illumination radiation to a sample that includes a fluorescent dye, a detector configured to obtain images of the sample by detecting light emitted from the sample, and an electronic processor configured to: obtain multispectral image information for the sample from one or more images obtained by the detector, the multispectral image information corresponding to an image cube that includes multiple two-dimensional layers, each layer corresponding to an image of the sample; calculate from the image cube a first spectrum that includes contributions from the endogenous fluorescence in the sample; calculate from the image cube a second spectrum that includes contributions from the fluorescent dye and from endogenous fluorescence in the sample; and calculate a pure spectrum of the fluorescent dye in the sample based on the first and second spectra, where a relative contribution of light emission from the fluorescent dye to the second spectrum is larger than a relative contribution of light emission from the fluorescent dye to the first spectrum, where calculating the first and second spectra includes identifying corresponding first and second sets of pixel intensity values in the image cube and using the identified sets of pixel intensity values to calculate the first and second spectra, and where identifying the first set of pixel intensity values includes designating one or more layers of the image cube as a first layer set, and identifying members of the first set of pixel intensity values based on the first layer set.

Embodiments of the system can include one or more of the following features.

The first spectrum can include contributions from the fluorescent dye. Relative contributions from light emission by other components in the sample can be reduced (and even minimized) in the pure spectrum of the fluorescent dye relative to the second spectrum.

The electronic processor can be configured, for each candidate pixel in the first layer set, to determine whether the pixel is a member of the first set of pixel intensity values based on a fraction of total pixel intensity that is attributable to the first layer set. The electronic processor can be configured to designate one or more layers of the image cube as a second layer set, and to identify members of the second set of pixel intensity values based on the second layer set. The electronic processor can be configured, for each candidate pixel in the first layer yet, to determine whether the pixel is a member of the first set of pixel intensity values based on a fraction of total pixel intensity that is attributable to the first layer set. The electronic processor can be configured, for each candidate pixel in the second layer set, to determine whether the pixel is a member of the second set of pixel intensity values based on a fraction of total pixel intensity that is attributable to the second layer set. The electronic processor can be configured to identify pixels that correspond to the sample based on the first set of layers.

The electronic processor can be configured to add the pure spectrum of the fluorescent dye to a spectral library, obtain a second set of multispectral image information for a second sample corresponding to a second image cube from one or more images obtained by the detector, where the second sample includes the fluorescent dye, and use the spectral library to unmix the second image cube to determine an amount of the fluorescent dye at multiple spatial locations in the second sample. The second sample can include a fluorescent counterstain, and the electronic processor can be configured to determine relative amounts of the fluorescent dye and the fluorescent counterstain at the multiple spatial locations in the second sample.

The electronic processor can be configured to determine the pure spectrum by subtracting from the second spectrum a scaled multiple of the first spectrum. The electronic processor can be configured to determine a value of a scaling coefficient that multiplies the first spectrum from pixel intensity values that correspond to multiple pixels in the image cube.

In a further aspect, the disclosure features methods that include: obtaining multispectral image information for a sample that includes a fluorescent dye, where the multispectral image information corresponds to an image cube that includes multiple two-dimensional layers, each layer corresponding to an image of the sample; designating at least one layer of the image cube as a first layer set corresponding to a dark band of the fluorescent dye; determining a first spectrum and a second spectrum based on respective first and second sets of pixel intensity values from the image cube; and calculating a pure spectrum of the fluorescent dye in the sample based on the first and second spectra and the first layer set, where a relative contribution of light emission from the fluorescent dye to the pixel intensity values is larger for the second set of pixel intensity values than for the first set of pixel intensity values.

Embodiments of the methods can include any one or more of the following features.

Relative contributions from light emission by other components in the sample can be reduced (and even minimized) in the pure spectrum of the fluorescent dye relative to the second spectrum. Calculating the pure spectrum can include minimizing contributions from the pure spectrum in the first layer set. Calculating the pure spectrum can include minimizing a sum of squared pixel intensity values in the first set of pixel intensity values. Calculating the pure spectrum can include minimizing a sum of absolute values of pixel intensity values in the first set of pixel intensity values.

The methods can include assigning a value of zero to contributions from the pure spectrum to pixel intensity values in the first layer set. The methods can include assigning a value of zero to negative intensity values in the pure spectrum of the fluorescent dye. The methods can include identifying pixels that correspond to the sample based on the first set of layers.

The methods can include adding the pure spectrum of the fluorescent dye to a spectral library, obtaining a second set of multispectral image information for a second sample corresponding to a second image cube, where the second sample includes the fluorescent dye, and using the spectral library to unmix the second image cube to determine an amount of the fluorescent dye at multiple spatial locations in the second sample. The second sample can include a fluorescent counterstain, and the methods can include determining relative amounts of the fluorescent dye and the fluorescent counterstain at the multiple spatial locations in the second sample.

The methods can include identifying the first and second sets of pixel intensity values based on the first layer set. The methods can include, for each candidate pixel in the first layer set, identifying members of the first set of pixel intensity values based on a fraction of total pixel intensity that is attributable to the first layer set. The methods can include designating at least one layer of the image cube as a second layer set corresponding to a light emission band of the fluorescent dye. The methods can include, for each candidate pixel in the first layer set, identifying members of the first set of pixel intensity values based on a fraction of total pixel intensity that is attributable to the first layer set. The methods can include, for each candidate pixel in the second layer set, identifying members of the second set of pixel intensity values based on a fraction of total pixel intensity that is attributable to the second layer set.

The methods can include determining the pure spectrum by subtracting from the second spectrum a scaled multiple of the first spectrum. The methods can include determining a value of a scaling coefficient that multiplies the first spectrum from pixel intensity values that correspond to multiple pixels in the image cube.

In another aspect, the disclosure features systems that include a radiation source configured to direct illumination radiation to a sample, a detector configured to obtain images of the sample by detecting light emitted from the sample, and an electronic processor configured to: obtain multispectral image information for a sample that includes a fluorescent dye from one or more images of the sample obtained by the detector, where the multispectral image information corresponds to an image cube that includes multiple two-dimensional layers, each layer corresponding to an image of the sample; designate at least one layer of the image cube as a first layer set corresponding to a dark band of the fluorescent dye; determine a first spectrum and a second spectrum based on respective first and second sets of pixel intensity values from the image cube; and calculate a pure spectrum of the fluorescent dye in the sample based on the first and second spectra and the first layer set, where a relative contribution of light emission from the fluorescent dye to the pixel intensity values is larger for the second set of pixel intensity values than for the first set of pixel intensity values.

Embodiments of the systems can include any one or more of the following features.

Relative contributions from light emission by other components in the sample can be reduced (and even minimized) in the pure spectrum of the fluorescent dye relative to the second spectrum. The electronic processor can be configured to calculate the pure spectrum by minimizing contributions from the pure spectrum in the first layer set. The electronic processor can be configured to calculate the pure spectrum by minimizing a sum of squared pixel intensity values in the first layer set. The electronic processor can be configured to calculate the pure spectrum by minimizing a sum of absolute values of pixel intensity values in the first layer set.

The electronic processor can be configured to assign a value of zero to contributions from the pure spectrum to pixel intensity values in the first layer set. The electronic processor can be configured to assign a value of zero to negative intensity values in the pure spectrum of the fluorescent dye. The electronic processor can be configured to identify pixels that correspond to the sample based on the first set of layers.

The electronic processor can be configured to: add the pure spectrum of the fluorescent dye to a spectral library; obtain a second set of multispectral image information for a second sample from one or more images obtained by the detector, the second set of multispectral image information corresponding to a second image cube, where the second sample includes the fluorescent dye; and use the spectral library to unmix the second image cube to determine an amount of the fluorescent dye at multiple spatial locations in the second sample. The second sample can include a fluorescent counterstain, and the electronic processor can be configured to determine relative amounts of the fluorescent dye and the fluorescent counterstain at the multiple spatial locations in the second sample.

The electronic processor can be configured to identify the first and second sets of pixel intensity values based on the first layer set. The electronic processor can be configured, for each candidate pixel in the first layer set, to identify members of the first set of pixel intensity values based on a fraction of total pixel intensity that is attributable to the first layer set. The electronic processor can be configured to designate at least one layer of the image cube as a second layer set corresponding to a light emission band of the fluorescent dye. The electronic processor can be configured, for each candidate pixel in the first layer set, to identify members of the first set of pixel intensity values based on a fraction of total pixel intensity that is attributable to the first layer set. The electronic processor can be configured, for each candidate pixel in the second layer set, to identify members of the second set of pixel intensity values based on a fraction of total pixel intensity that is attributable to the second layer set.

The electronic processor can be configured to determine the pure spectrum by subtracting from the second spectrum a scaled multiple of the first spectrum. The electronic processor can be configured to determine a value of a scaling coefficient that multiplies the first spectrum from pixel intensity values that correspond to multiple pixels in the image cube.

Embodiments of the methods and systems can also include any of the other features disclosed herein, including features disclosed in connection with different embodiments, in any combination as appropriate.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Introduction

Figure 1:
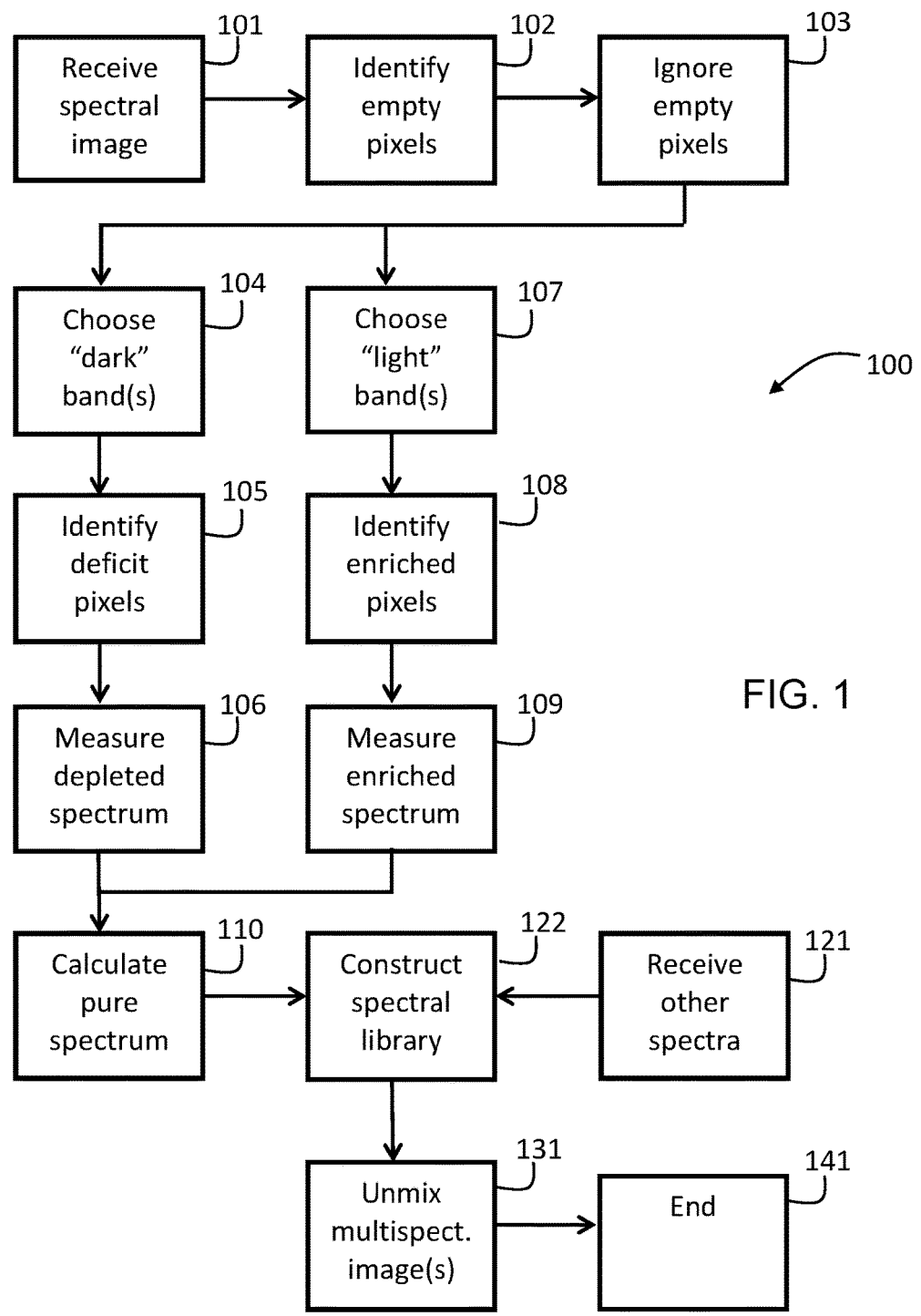
FIG. 1 is a flow chart that includes a series of steps for calculating a pure spectrum of a fluorescent dye in a sample.

It is possible to unmix the spectrum at each position of an image cube into its various component signals, using a spectral library of known spectra for the components that are present in the sample. Nuance® software from PerkinElmer (Waltham, Mass.) (hereinafter "Nuance®") can produce such spectral libraries and use them to unmix image cubes into component images. Techniques for unmixing multi-spectral images (e.g., image cubes) are described, for example, in U.S. Pat. No. 8,391,961, U.S. Pat. No. 8,634,607, and U.S. Pat. No. 8,462,981, which further explain how to obtain an estimate for the pure spectrum of a fluorescent dye, based on a measured spectrum containing a mixture of signals from the dye and another component (such as autofluorescence), and an estimate for the pure spectrum of the other component. The entire contents of each of the foregoing patent documents are incorporated herein by reference.

Spectral unmixing is also useful when performing classification or image analysis. Suitable methods for classifying images are described, for example, in U.S. Pat. No. 7,953,264 and U.S. Pat. No. 8,103,081. The entire contents of each of the foregoing patent documents are incorporated herein by reference.

It has been reported (see, for example, James R. Mansfield, "Imaging in cancer immunology: phenotyping immune cell subsets in situ in FFPE tissue sections," *European Journal of Cancer* Vol. 51, Supp. 1, p. S2 (2015)) that sequential staining can be used to label tissue samples with up to 8 antibody-labeled fluorescent probes, plus a 4',6-diamidino-2-phenylindole (DAPI) fluorescent nuclear counterstain. This provides information that can be of great value when phenotyping immune cells to gauge how a patient's immune system is responding to cancer or another disease, or when measuring protein expression of various markers, or to do both in the same sample.

The present disclosure features systems and methods for determining the spectrum of a fluorescent dye based on cell or tissue samples that contain the dye and also may exhibit fluorescence from other entities, including other dyes, and sample autofluorescence. The systems and methods can determine the dye spectrum to produce a result that is indicative of the true dye spectrum as it would appear in the absence of sample autofluorescence, and which is substantially unaffected by the presence of autofluorescence, or its detailed properties.

When different points in a sample exhibit fluorescence with different proportions of autofluorescence signal and dye signal, it is possible to produce a reliable estimate of the pure dye spectrum by careful analysis of the difference between spectra corresponding to relatively dye-enriched and relatively dye-deficient locations in the sample. Particularly, the spectral difference between the two describes the effect of changing the relative proportion of dye and autofluorescence. The systems and methods disclosed herein use this difference to synthetically "purify" a spectrum taken from an unknown mixture of both components.

One aspect of determining the pure spectrum of the fluorescent dye is determining how much to "purify" the measured spectrum, though the relative proportions (and contributions) of dye and autofluorescence to the measured spectrum are unknown, and the effect of adding (or subtracting) a given amount of the spectral difference signal is not known. The systems and method disclosed herein address this difficulty by subtracting a selected amount of the difference spectrum, where the selection is made based on a minimal amount of a priori knowledge about the dye and the autofluorescence.

Preferably, the a priori knowledge about the dye includes two features: first, a "dark" band, which is a combination of excitation and emission wavelengths for which the dye is known to exhibit little or no fluorescence; and second, a "light" band, which is a combination of excitation and emission wavelengths for which the dye is known to exhibit significant fluorescence (though it need not be the brightest of all possible combinations).

There is only one piece of a priori knowledge about the autofluorescence that is used, namely, that it have some non-zero emission in the dye's dark band. The dark band emission need not be the brightest point in the autofluorescence spectrum, provided that it is sufficiently strong to be measurable.

In some embodiments, two sets of pixels are selected, one of which is relatively enriched in the dye compared with the other. For a pixel that is "enriched" in the dye, a greater proportion of the total emission light intensity for the pixel is attributable to the dye relative to endogenous fluorescence (including autofluorescence), relative to a pixel that is not enriched or "deficient" in the dye, where a lesser proportion of the total emission light intensity for the pixel is attributable to the dye relative to endogenous autofluorescence.

Note that for both sets of pixels (i.e., both dye-enriched pixels and dye-deficient pixels), fluorescence emission from the dye can provide the major contribution to the total light emission intensity, and autofluorescence the minor contribution to the total intensity, so emission light from the dye dominates in both populations, which differ only in the relative proportions of dye fluorescence and autofluorescence. Alternatively, in some implementations, autofluorescence can constitute the majority contribution to the total emission intensity at both dye-enriched and dye-deficient pixels, with a smaller relative contribution to the total emission intensity of dye-enriched pixels. As another alternative, in certain implementations, the spectra of dye-enriched pixels can include primarily light emission from the fluorescent dye, and the spectra of dye-deficient pixels can be primarily or entirely composed of autofluorescence light emission. Any of these scenarios is amenable to analysis, provided that the two pixel populations differ in the relative proportions of contributions from dye and autofluorescence in their overall measured light emission.

The methods and systems disclosed herein determine an estimate of the pure dye spectrum of a fluorescent dye (or, more generally, a fluorescent emitter in a sample) based on the dye-enriched pixels' spectrum minus some amount of the dye-deficit pixels' spectrum. The exact amount of dye-deficit spectrum to subtract is adjusted as necessary to obtain a mean value of zero in the "dark band". The resulting spectrum is a good estimate of the true dye spectrum. Optionally, the contributions from the estimate of the pure spectrum can then be set to exactly zero in the spectrum "dark band", or negative values anywhere in the spectrum can be adjusted to zero, or both.

The systems and methods disclosed herein are considerably simpler than other methods for determining dye spectra. They do not depend upon an independent measurement of the pure autofluorescence spectrum, which is conventionally done via a "witness" sample that is dye-free but otherwise comparable to the dye-bearing sample, and do not depend upon complete identification of dye-free points within the dyed sample.

Either of these brings complexity, operator-dependence, measurement error, or some mixture of these. Using a witness sample adds complexity, since it requires obtaining a suitable tissue section and preparing it properly. Further, it may not be convenient (or possible) to obtain a witness sample for which the autofluorescence spectrum is a good match to that of the dyed sample. If so, accuracy will be degraded for measurements that rely on this trait. Choosing points in an image of the dyed sample that are dye-free typically involves operator judgment that may not be reliable, and may vary from one operator to another. Thus one expects the results to vary based on operator skill, training, and/or random choices made during the analysis.

In contrast, the methods and systems disclosed herein can operate with a single sample wherein every point contains a mixture of dye and autofluorescence contributions. Also the dye spectrum it produces is not degraded by the presence of autofluorescence everywhere in the sample, or by ubiquitous (non-specific) binding of the dye. Moreover, the measurements of the dye spectra are indicative of the dyes themselves, rather than operator skill or peculiarities of the sample used to make the measurement. The methods and systems disclosed herein can provide determinations of spectra that are partially or fully automated so that operator skill and judgment are minimal, and measurements are highly reproducible across all operators. Similarly, the same operator would obtain similar results from repeated measurements of the same sample, or measurements of multiple, comparable samples prepared with the same dye.

A further aspect of the methods and systems disclosed herein is that measurements of spectra can be repeated as a quality or consistency check on the histology preparation used for samples. For example, dye spectra can be checked at regular intervals, or to qualify a new lot of chemicals, or to validate proposed changes to the histology protocol, or to compare staining processes at different laboratory sites.

Because the methods and systems provide a determination of the spectral properties of the dye that is substantially independent of the autofluorescence of the sample which contains it, and the determination is largely automated and operator-independent, if differences are noted, they are more likely to indicate actual changes in the histology, and less likely to be false alarms arising from confounding influences or measurement error, than is generally observed when using other, conventional methods.

The systems and methods disclosed herein can also be used to provide measurements of spectra that are suitable for multispectral analysis of cell and tissue samples that contain a large number of exogenous fluorescent dyes, such as 4 fluorescent probes and a counterstain, or 5 fluorescent probes and a counterstain, or even 6 or more fluorescent probes and a counterstain. In all these cases, there may also be autofluorescence arising from the sample. Reliable spectra are increasingly important as the number of dyes is increased, or when multiple dyes are used having spectra that are similar or overlap to a great degree.

In general, the systems and methods disclosed herein analyze spectra associated with fluorescent spectral images of cell and tissue samples. These contain images of samples taken at multiple excitation wavelengths, emission wavelengths, or different combinations of the two. One can represent this kind of information as being an image cube, meaning a multi-layer image, where each layer contains one of the images of the sample, and the collection of values $S_i$ for the N layers at each pixel form a spectrum S for that location in the sample. S can be seen as a vector in N-space.

Often such signals are reported in somewhat arbitrary units such as digital counts detected by the instrument that acquired the images, which may not be calibrated in terms of SI units or any other absolute measurement scale. The systems and methods disclosed herein do not require such calibrations to successfully analyze multispectral image information, but can analyze calibrated information if it is available. Another common practice in multispectral imaging is to scale the signals in the image cube by the exposure time, camera gain, or other factors related to the acquisition conditions in a known way, to make it easy to compare images taken using different settings or to use spectra obtained under one set of exposure and gain conditions to unmix an image obtained under different conditions. The systems and methods disclosed herein can analyze such scaled information.

Analysis of Multispectral Image Information

An important concept in multispectral imaging is that of a normalized spectral vector s, collinear with S but having unit Cartesian length:

$$s = \frac{S}{|S|} = \frac{S}{\sqrt{S_1^2 + S_2^2 \ldots + S_n^2}} \quad [1]$$

The normalized vector s indicates the direction of a spectrum vector S in N-space. Each pixel in an image cube may be described by its (x, y) sample location and spectrum S; the latter can be decomposed into a signal strength |S|, and a spectral direction vector s.

Another useful concept is that of a dark band spectrum $S_{dark}$, corresponding to a spectrum S with all its elements $S_i$ set to zero except in a "dark" band where the dye is known not to fluoresce. Similarly, $s_{dark}$ corresponds to s with all but "dark" band elements set to zero. Note that $s_{dark}$ is not, in general, a unit length vector; because only selected elements of a normalized spectrum were retained, its length indicates how much of the spectrum s was in the "dark" band.

A related concept is that of a light band spectrum $S_{light}$, corresponding to S with all elements $S_i$ set to zero, except in the "light" band where the dye is known to fluoresce. Similarly, $s_{light}$ denotes s with all but the "light" band elements set to zero. Like $s_{dark}$, its length is not always 1, but instead varies depending on how much of s was in the "light" band.

FIG. 1 is a flow chart 100 that shows a series of steps for analyzing multispectral image information (e.g., in the form of a spectral image cube) to determine a pure spectrum of a fluorescent dye in a sample. A spectral image is received in step 101, either directly from an instrument that can acquire a suitable spectral image cube, or from another source such as a disk drive, network, or computer that has access to spectral image information that has been already acquired.

The image is a spectral image cube containing fluorescent signal measurements of a sample (e.g., a tissue or cellular sample). Certain regions of the image may be empty, meaning they contain an insignificant amount of sample material, or none at all. In the following discussion, the sample is a breast cancer sample obtained as a formalin-fixed, paraffin-embedded (FFPE) tissue block, from which a 4 micron section was cut with a microtome, and then subjected to standard histology processes for dewaxing, antigen retrieval, and immuno-fluorescent (IF) labeling using an ER probe conjugated to Alexa® 488 dye (available from Life Sciences Solutions, Carlsbad, Calif.), and mounted on a standard microscope slide with a cover slip. More generally, however, a wide variety of different samples can by imaged and analyzed using the systems and methods disclosed herein.

A spectral image of this sample was obtained using a Vectra® multispectral imaging system (available from PerkinElmer, Waltham, Mass.). It incorporates a digital camera attached to an Olympus BX51 microscope with epi-illumination optics. The latter provides a filter wheel that accepts up to 6 epi-filter cubes, with motorized control. The wheel is populated as shown in Table 1 for all the examples described herein. By changing which filter is engaged, one selects what wavelength of excitation light is provided to the sample, and what range of emission wavelengths are presented for imaging by the digital camera. Optionally a liquid crystal tunable filter (LCTF) can be engaged in front of the camera to select a subset of emission wavelengths within the emission band, which can be swept to provide an emission spectrum.

TABLE 1

| Filter # | Name | Manuf. | Part Number | Excitation | Emission |
|---|---|---|---|---|---|
| 1 | Bright-field | — | — | — | — |
| 2 | DAPI | Semrock | DAPI-50LP-A-000 | 352-402 nm | 409 nm LP |
| 3 | FITC | Chroma | 49012 | 460-500 nm | 510 nm LP |
| 4 | Cy3 | Chroma | 41032 | 530-560 nm | 572 nm LP |
| 5 | Texas Red | Semrock | mCherry-40LP-A-000 | 542-582 nm | 593 nm LP |
| 6 | Cy5 | Chroma | 49006 | 590-650 nm | 662-738 nm |

The system used to capture multispectral image information is configured to acquire spectral images that enable distinguishing the dye spectrum from the autofluorescence spectrum in the samples being used. In some embodiments, the systems can use a single epi-filter element or several such filters. In certain embodiments, the systems can be configured to capture several images with each epi-filter, using a spectral selection element like an LCTF to obtain more spectral information, or not. The choice of imaging modality and optical elements in the system typically depends upon the nature of the sample at hand.

For the sample discussed above, an image cube with 23 layers was acquired using the Vectra® system, with the epi-cube filters, emission wavelengths, and exposure times as listed in Table 2. The image cube signals were measured in digital count units with no scaling applied for exposure time or gain.

TABLE 2

| Layer | Epi Filter | Wavelength (nm) | Exposure Time (ms) Initial Example Examples 2, 4 | Exposure Time (ms) Example 1 | Exposure Time (ms) Example 3 |
|---|---|---|---|---|---|
| 1 | DAPI | 440 | 14 | 9 | 8 |
| 2 | DAPI | 460 | 14 | 9 | 8 |
| 3 | DAPI | 480 | 14 | 9 | 8 |
| 4 | DAPI | 500 | 14 | 9 | 8 |
| 5 | DAPI | 520 | 14 | 9 | 8 |
| 6 | DAPI | 540 | 14 | 9 | 8 |
| 7 | DAPI | 560 | 14 | 9 | 8 |
| 8 | DAPI | 580 | 14 | 9 | 8 |
| 9 | DAPI | 600 | 14 | 9 | 8 |
| 10 | FITC | 480 | 925 | 925 | 925 |
| 11 | FITC | 500 | 925 | 925 | 925 |
| 12 | FITC | 520 | 925 | 925 | 925 |
| 13 | FITC | 540 | 925 | 925 | 925 |
| 14 | FITC | 560 | 925 | 925 | 925 |
| 15 | FITC | 580 | 925 | 925 | 925 |
| 16 | FITC | 600 | 925 | 925 | 925 |
| 17 | Texas Red | 580 | 126 | 126 | 126 |
| 18 | Texas Red | 600 | 126 | 126 | 126 |
| 19 | Texas Red | 620 | 126 | 126 | 126 |
| 20 | Texas Red | 640 | 126 | 126 | 126 |
| 21 | Texas Red | 660 | 126 | 126 | 126 |
| 22 | Texas Red | 680 | 126 | 126 | 126 |
| 23 | Texas Red | 700 | 126 | 126 | 126 |

Figure 2A:
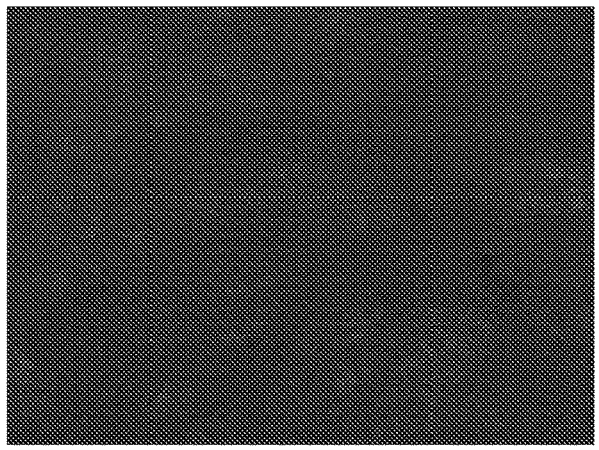
FIGS. 2A-2C are images showing blue, green, and red planes, respectively, of a color rendering of an image cube with 23 spectral layers corresponding to an image of a breast-cancer sample that was prepared with a probe that targets estrogen receptor (ER) using a fluorescent dye.
Figure 2B:
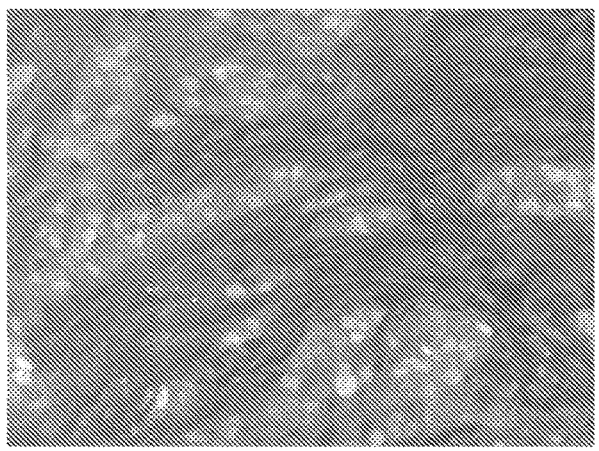
Figure 2C:
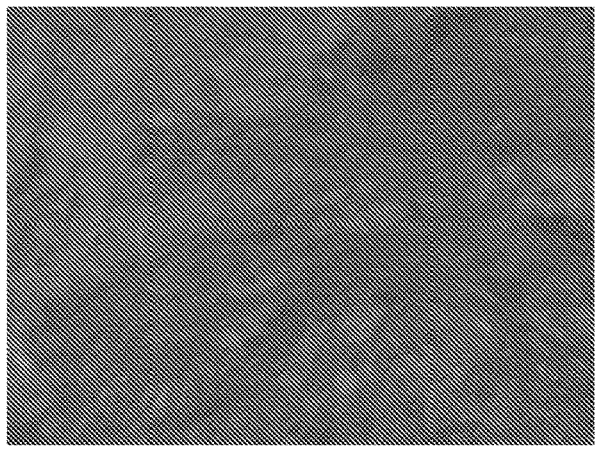

A color image of this cube was rendered using inForm® 3.0.2 software (available from PerkinElmer, Waltham, Mass.), and the blue, green, and red planes of this image are shown in FIGS. 2A-2C, respectively. A representative region of interest was extracted from the image cube, consisting of the central 696×520 pixel region within the original 1392× 1040 image, and the rest was discarded.

Next, optional steps 102 and 103 were performed, in which empty regions were identified and the associated empty pixels are marked to be ignored in all subsequent steps. The empty regions were identified by constructing an image of the "dark" band signal $S_{dark}$ for the image cube and marking pixels with weak signal as empty, or blank.

Alexa® 488 stain fluoresces very weakly when excited with light in the 352-402 nm range produced by the DAPI filter cube, and not at all when excited with light in the 550-575 nm range produced by the Texas Red epi-filter cube. All image layers acquired with either of these epi-filters were considered to be the "dark" band for the present sample. Conversely, all image layers acquired with the FITC filter cube were considered to be the "light" band, since Alexa® 488 fluoresces intensely when exposed to light in the 450-490 nm range produced by this filter.

It is instructive to consider the physical meaning of the dark-band signal $|S_{dark}|$. Since this term considers only contributions from dark-band layers, little or none of the signal is coming from Alexa® 488 in the sample; it is largely or entirely attributable to sample autofluorescence. Thus the distribution of $|S_{dark}|$ across the image indicates the distribution of autofluorescence in the sample, which enables the location of regions of tissue or cell material.

Figure 3:
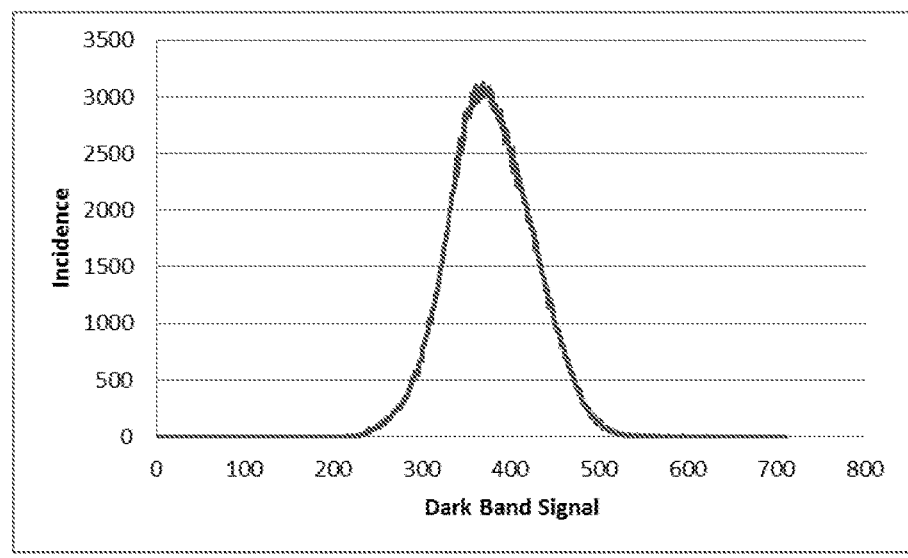
FIG. 3 is a plot showing a histogram of the signal strength of image pixels across a dark band of a fluorescent dye, corresponding to layers of a spectral cube acquired with or Texas Red epi-filters.
Figure 4:
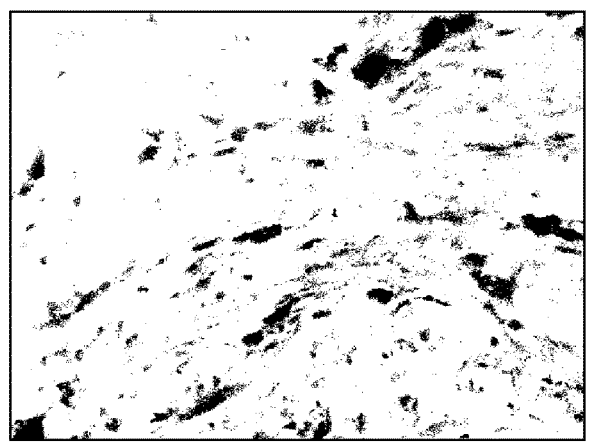
FIG. 4 is an image showing a binary mask of the images of FIGS. 2A-2C, in which regions where tissue is present appear white, and regions where there is no tissue material present are black.

A histogram of the signal strengths $|S_{dark}|$ for the 520×696 image region is shown in FIG. 3. Based on this, a threshold was set to 313 counts, below which a pixel was considered empty. The resulting mask is shown in FIG. 4, where blank pixel regions are shown in black.

Such a determination is rarely if ever perfect. If the threshold is set too low, subsequent steps will include pixels from sample-free regions. Alternatively, if the threshold is set too high, subsequent steps will exclude some sample-bearing pixels. The consequences of this will be discussed in greater detail subsequently.

While this example finds empty regions based on a threshold applied to $|S_{dark}|$, other approaches can be used instead, so long as they are suitable for locating where there is sample material and where there is not, for the type of samples at hand.

In some cases, the image cube may contain regions with dust, contamination or other foreign material, or large blank regions. For reasons such as this, it is helpful to provide a way for a user to define regions that should be ignored. User intervention of this type may occur before or after steps 102 and 103. Other than this, no user interaction generally occurs, and the determination of the dye spectrum is completely automatic.

In step 107, the "light" bands are selected. In this example, the light bands correspond to the image cube planes for which the FITC epi-filter was used during acquisition. In step 104, the "dark" bands are selected. In this example, the dark bands correspond to the image cube planes for which DAPI or Texas Red epi-filters were used during acquisition.

In general, membership in the "dark" and "light" bands are mutually exclusive traits, because they represent incompatible properties: the former means the dye is known a priori to express little or no fluorescence, while the latter means the dye is known to exhibit significant fluorescence. Thus no point $S_i$ in the spectrum can properly be assigned to both bands.

However, the two are not complementary: the combination of the dark and light bands need not form the entire spectrum S. Put another way, a point $S_i$ in the spectrum need not be assigned to either the dye band or the dark band. For example, there may be spectrum points for which one has no a priori knowledge that there is either significant fluorescence, or substantially no fluorescence. Such spectral points would be assigned to neither band.

In step 108, pixels were selected as being relatively enriched in the dye signal by calculating an image whose pixel values were given by $|s_{light}|$ and choosing the pixels whose signal was larger than a particular threshold value (in this example, pixels whose signal was in the 98$^{th}$ percentile or higher of intensity signals). This selects for pixels that contained a relatively higher proportion of their signal in the dye bands, compared with other pixels.

Figure 5A:
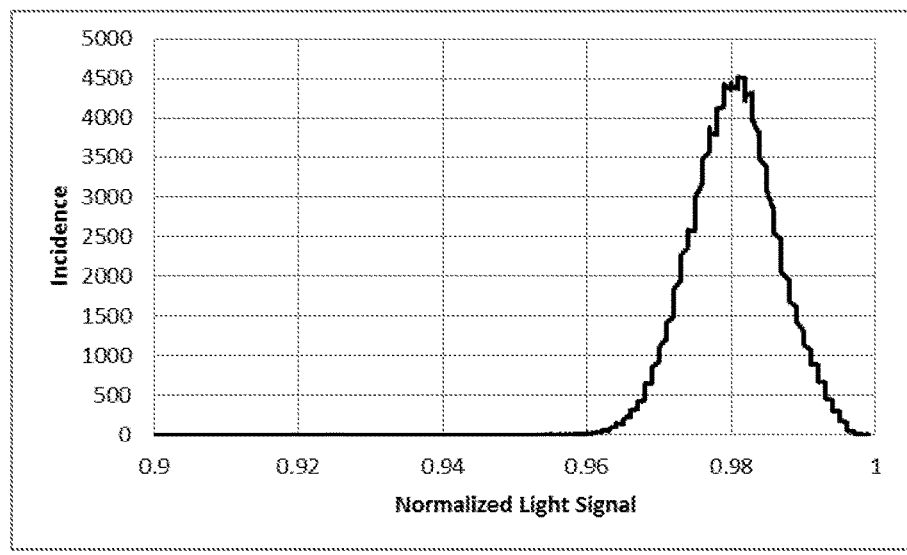
FIG. 5A is a plot showing a histogram of pixels in the non-blank regions of the image in FIGS. 2A-2C, ranked by normalized signal strength in the light band, in which the fluorescent dye is expected to exhibit fluorescence.

It is helpful to explain why this is so. Recall that $s_{light}$ are normalized spectra s for which all entries si except the dye band entries have been set to zero. Taking normalized spectra eliminates the effect of overall pixel brightness, leaving only spectral composition as a basis for selection. Then, ranking pixels in terms of the contribution of the dye bands alone provides a convenient way to select pixels based on the proportion of dye fluorescence to total fluorescence. The property $|s_{light}|$ provides a convenient way to perform just such a ranking. FIG. 5A shows the histogram of pixels ranked by $|s_{light}|$.

A mask was then constructed of all pixels meeting the 98% criterion for $|s_{light}|$, and 1000 pixels were randomly chosen from within this mask, as examples of pixels whose signal was relatively enriched in dye fluorescence. In step 105 of FIG. 1, the same mask was used to exclude dye-enriched pixels from the general group of non-empty pixels, producing a group of pixels that were neither empty, nor deemed to be dye-enriched.

Figure 5B:
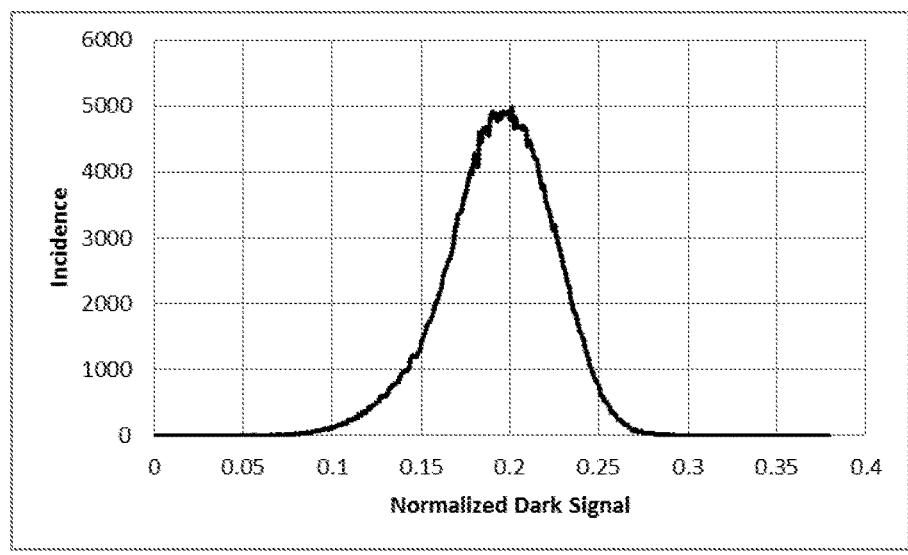
FIG. 5B is plot showing a histogram of the same pixels in FIG. 5A, ranked by normalized signal strength in the dark band.

For these pixels, $|s_{dark}|$ was calculated, and FIG. 5B shows the histogram ranking these pixels in terms of $|s_{dark}|$. Pixels which rank highest in this band have the greatest proportion of their signal coming from sources other than the dye, so they are expected to be dye-deficit. A subset of the pixels was chosen based on a threshold (the 80% point in the $|s_{dark}|$ histogram was chosen as the threshold, and 1000 pixels were randomly chosen from among those meeting or exceeding this threshold) as examples of pixels that were relatively deficient in dye fluorescence.

Figure 6A:
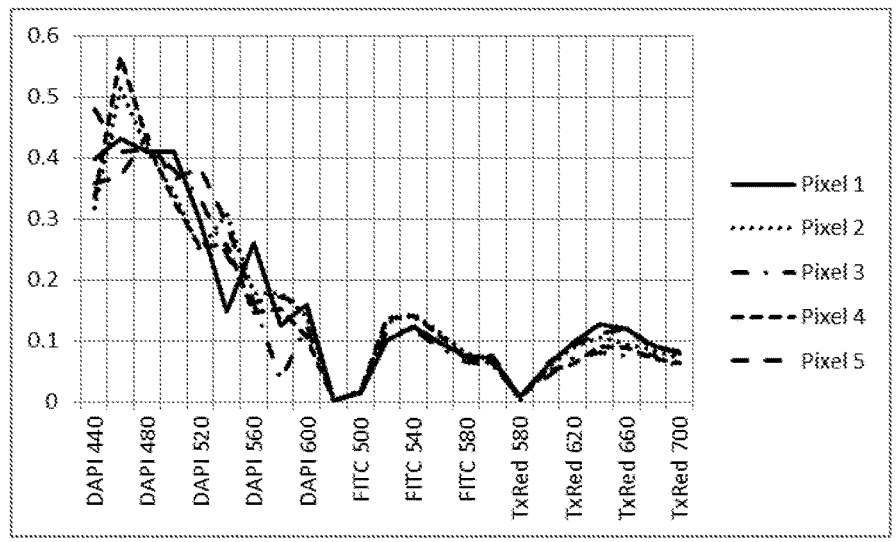
FIG. 6A is a plot showing normalized spectra for a set of pixels selected as being preferentially enriched in a fluorescent dye.
Figure 7A:
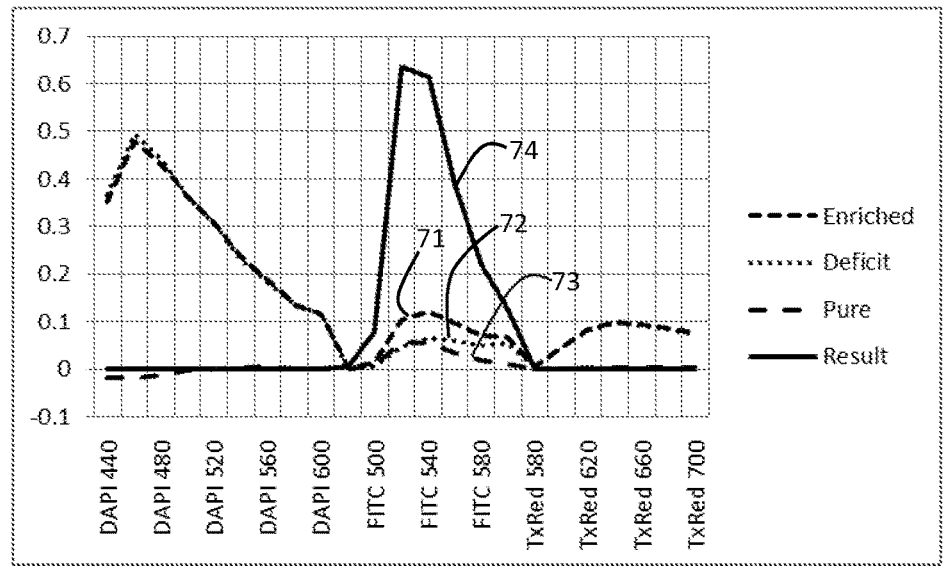
FIG. 7A is a plot showing the mean signal for preferentially dye-enriched pixels, the mean signal for dye-deficit pixels, the spectrum that was determined for the pure fluorescent dye, and the fluorescent dye spectrum after setting the dark band elements to zero and normalizing to unit length.

Next, in step 109 of FIG. 1, the mean spectrum for the dye-enriched pixels was obtained by summing the s vectors for each of those pixels, and dividing by the number of pixels. Spectra for individual dye-enriched pixels are shown in FIG. 6A, and the mean dye-enriched spectrum is shown as curve 71 in FIG. 7A.

Figure 6B:
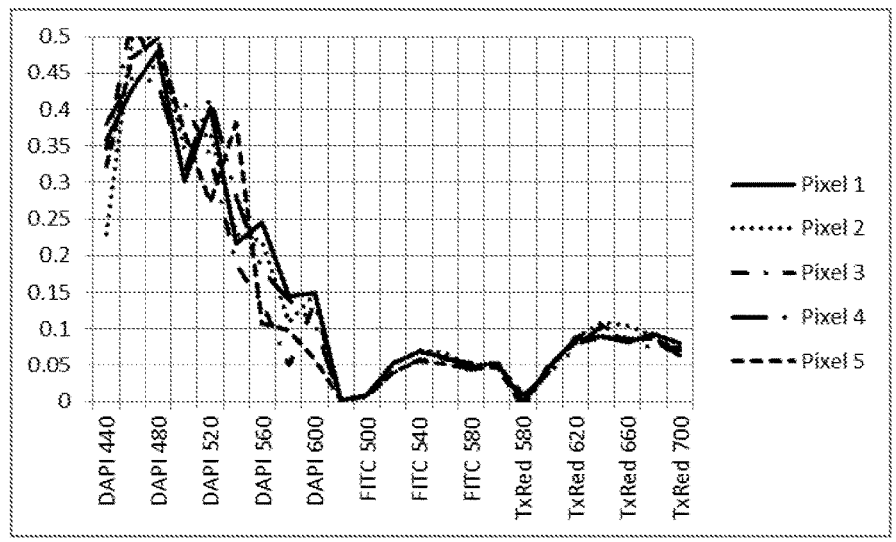
FIG. 6B is a plot showing normalized spectra for a set of pixels selected less enriched, or in deficit, in the fluorescent dye relative to the pixels of FIG. 6A.

Then, in step 106 of FIG. 1, the mean spectrum for the dye-deficit pixels was obtained in a similar way, using s for the set of dye-deficient pixels. Spectra for individual dye-deficient pixels are shown in FIG. 6B, and the mean dye-deficit spectrum is shown as curve 72 in FIG. 7A.

In this example the dye-enriched pixels were chosen first, and this selection was used to perform the selection of dye-deficit pixels, namely by creating a mask of all dye-enriched pixels and excluding these from the possible dye-deficit pixel set. In general, however, the operations in steps 105 and 108 need not be coupled. In some embodiments, for example, they can be performed independently. For example, the dye-enriched mask was not constructed prior to choosing the dye-deficient pixels, but the dye-deficient pixels were instead selected from among all non-empty pixels, the two operations would be independent. Depending on the samples at hand and the thresholds chosen, either approach can be used. In addition, steps 105 and 108 can be performed in any order, or in parallel.

The pure dye spectrum is calculated from the mean enriched spectrum 71 and the mean deficit spectrum 72 (shown in FIG. 7A) based on the a priori knowledge that Alexa® 488 has little or no fluorescence in the dark band.

Signals were scaled by the exposure time from this point forward in the calculations. For example, a signal of 82 counts in the first layer of the image cube, acquired at 440 nm with the DAPI epi-filter and an exposure of 14 ms, would be 5857 counts per second after scaling.

Next, in step 110, the pure spectrum is calculated. Physically, the dye-enriched spectrum indicates a signal that is a mixture of some dye fluorescence and an unknown amount of autofluorescence, and the dye-deficit spectrum indicates a different mixture of the two, in which there is relatively lower proportional amount of dye fluorescence. This can be expressed algebraically as:

$$\begin{bmatrix} a_{11} & a_{12} \\ a_{21} & a_{22} \end{bmatrix} \begin{bmatrix} s_{Dye} \\ s_{AF} \end{bmatrix} = \begin{bmatrix} s_{Enriched} \\ s_{Deficit} \end{bmatrix}, a_{11} > a_{21} \quad [2a]$$

This captures the underlying assumptions in the model: that the sample can be described as a two-component system having dye and autofluorescence components; that these have spectra $s_{Dye}$ and $s_{AF}$ respectively; and that the measured spectra $s_{Enriched}$ and $s_{Deficit}$ contain different amounts of these components, given by coefficients $a_{ij}$.

Equation (2a) can be rewritten as:

$$A\,C = M \quad [2b]$$

where C denotes the column vector of component spectra $s_{Dye}$ and $s_{AF}$; A denotes the coefficient values $a_{ij}$; and M denotes the column vector of measured spectra $s_{Enriched}$ and $s_{Deficit}$.

Solving Equation (2b) for C yields the pure spectra for the dye fluorescence and autofluorescence, in isolation from one another:

$$C = A^{-1} M \quad [3a]$$

$$\begin{bmatrix} s_{Dye} \\ s_{AF} \end{bmatrix} = \begin{bmatrix} a_{11}^{-1} & a_{12}^{-1} \\ a_{21}^{-1} & a_{22}^{-1} \end{bmatrix} \begin{bmatrix} s_{Enriched} \\ s_{Deficit} \end{bmatrix} \quad [3b]$$

In general, one cannot invert A to obtain $A^{-1}$, since its coefficients $a_{ij}$ are unknown. But one can nonetheless solve for the upper row, or at least for the ratio of its two elements, as follows. Expanding Equation (3b) for the top row yields:

$$s_{Dye} = a_{11}^{-1} s_{Enriched} + a_{12}^{-1} s_{Deficit} \quad [4]$$

Of course, since this is true for the entire spectrum, it is true for any portion of the spectrum, such as the portion that constitutes the dark band. Thus:

$$s_{Dye(dark)} = a_{11}^{-1} s_{Enriched(dark)} + a_{12}^{-1} s_{Deficit(dark)} \quad [5]$$

However, by a priori knowledge the dye has substantially no fluorescence in the dark band, so:

$$0 = s_{Dye(dark)} = a_{11}^{-1} s_{Enriched(dark)} + a_{12}^{-1} s_{Deficit(dark)} \quad [6a]$$

$$a_{12}^{-1} s_{Deficit(dark)} = -a_{11}^{-1} s_{Enriched(dark)} \quad [6b]$$

$$a_{12}^{-1} = -a_{11}^{-1} \frac{s_{Enriched\,(dark)}}{s_{Deficit\,(dark)}} = -a_{11}^{-1} \lambda \quad [6c]$$

Here $\lambda$ is a scalar that represents the ratio of the signal level in the dark band of the dye-enriched spectrum to that in the dye-deficit spectrum. If the underlying assumptions stated in Equation (2a) held exactly, this would be true for each and every element in the dark band, viz:

$$\lambda = \frac{s_{i\,Enriched}}{s_{i\,Deficit}} \quad [7]$$

for any i corresponding to an element in the dark band of the spectrum.

Thus, one can calculate a spectrum $S_{Dye}$ from the measured values for $s_{Enriched}$ and $s_{Deficit}$ using Equation (5), (6b), and (7):

$$S_{dye} = s_{Enriched} - s_{Deficit} \frac{s_{i\,Enriched}}{s_{i\,Deficit}} = s_{Enriched} - \lambda s_{Deficit} \quad [8]$$

According to Equation (8), the desired pure dye spectrum can be obtained by subtracting a selected amount $\lambda$ of the measured spectrum of dye-deficit pixels from the measured spectrum of dye-enriched pixels, and the value of $\lambda$ is given by the ratio of the dye-enriched spectrum to that of the dye-deficit spectrum, within the dark band that was defined based on a priori knowledge about the dye. The spectrum $S_{dye}$ from Equation (8) is not normalized to unit length, but $s_{dye}$ is readily obtained from it using Equation (1), if that is desired.

As discussed above in connection with Equation (7), $\lambda$ can be obtained from a single element in the dark band, but in practice it is preferable to calculate this parameter in a way that is tolerant of measurement error. In the present example, λ was determined by calculating the ratio of the summed signal levels in all dark-band elements i, rather than just one element. That is, in step 110, the pure spectrum $S_{dye}$ is calculated using Equation (8), where λ was calculated as:

$$\lambda = \frac{\sum_{dark} s_{i\ Enriched}}{\sum_{dark} s_{i\ Deficit}} \quad [9]$$

This produces a mean signal of zero in the dark-band of $S_{dye}$ and was observed to give good results in all subsequent processing, as further described below.

One can view this as imposing a constraint on the pure spectrum, namely that its mean signal is zero in the dark band. Other criteria can be used as well, such as choosing 2 to minimize the absolute value of the pure spectrum signal, summed across the dark band; or to minimize the squared signal, summed across the dark band. These produced broadly similar results to those of Equation (9), and other criteria can be used if desired to achieve the general objective of a low signal level in the dark band, using some chosen criterion for what it means that the signal be low.

Also as part of step 110, the spectrum elements $S_i$ for the dye estimate were set to zero for all elements i in the dark band. This can be used to achieve several aims, at once. First the dye is known a priori to have little or no fluorescence emission in this band, so it is appropriate to force them to zero. Second, this eliminates negative values, which are logically inconsistent. Yet negative numbers are nearly inevitable whenever the dark band contains 2 or more elements and λ is calculated via any of the criteria listed above (mean signal of zero, minimize sum of absolute signal, minimize sum of squared signal).

In general, the signal is not identically zero across the dark band. This could arise from measurement noise, which is reduced but not eliminated by looking at the properties of a set of pixels to gain more statistical weight. However, there can be other reasons as well. The systems and methods disclosed herein use a single image to estimate two populations, having greater and lesser contributions from dye and autofluorescence signals, and then calculate the spectral difference between them to remove autofluorescence from the spectrum of the former population, under a constraint related to a priori knowledge about the dye signal in the dark band.

Thus a difference between two spectra is used to remove an unwanted signal that is presumed to be shared by both. To the extent that the dye-deficit pixels contain material that has a different species of autofluorescence, with a different spectrum from that contributing to the dye-enriched pixels, an imperfect estimate will be obtained because of that difference.

The systems and methods disclosed herein benefit from the fact that same sample is used in both cases. Thus the sample fixation, histology, mounting, and imaging processing are alike. This stands in contrast to the situation with other techniques that use a separate autofluorescence "blank" to obtain an estimate for that signal. In such methods, it is inevitable that there will be some difference in the tissue itself; at best, adjacent sections are available, but in practice that may not be possible so tissue from a different tissue block might be used for reasons of convenience, or limited access to the block with the dye and probe, or due to other factors.

Notwithstanding this benefit, the autofluorescence signal that contributes to the dye-enriched pixels may differ slightly from that contributing in the dye-deficit pixels. Without wishing to be bound by theory, this may be due to inherent sample variability giving rise to different molecular composition between different cell compartments (nuclear, cytoplasmic, and membrane), or between different tissue structures (stroma, epithelium, vessels, and so on), or between that of the intended sample material and other material in the scene (red blood cells, debris).

Further, any strategy for selecting a dye-enriched set of pixels and a dye-deficit set of pixels is vulnerable to statistical selection pressures that may favor one species of autofluorescence over another, if differing species exist. For example, by taking pixels based on a high rank in a histogram that ranks pixels by dark band component signal $|s_{dark}|$, one imposes statistical bias in favor of pixels whose autofluorescence spectrum is strong in that band. Thus the pixels chosen to be dye-deficit may inherently provide a somewhat unrepresentative autofluorescence signal component, as well.

This type of effect is reduced by choosing from among a relatively broad population of dye-deficit candidates, rather than from a narrower group that might be expected to be less representative and contain a greater proportion of outliers. In the example discussed above, the dye-deficit pixel set was chosen based on an 80% histogram level.

The pure spectrum of the dye obtained according to the methods discussed above is shown as curve 73 in FIG. 73, prior to setting dark band signals to zero, and as curve 74 after doing so and normalizing to unit length.

Figure 7B:
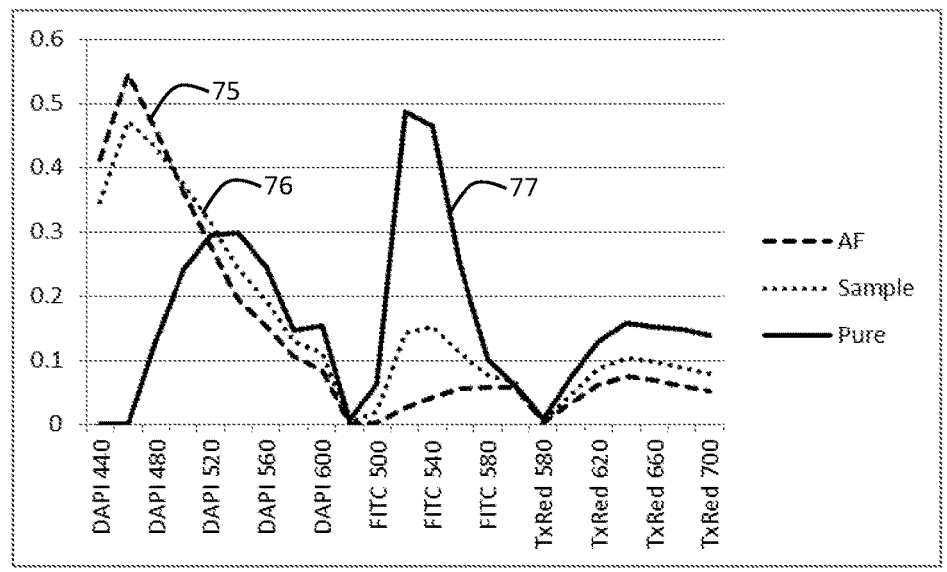
FIG. 7B is a plot showing shows the calculated spectrum for the fluorescent dye in the sample of FIGS. 2A-2C, the mixed (dye and autofluorescence) spectrum, and the pure autofluorescence spectrum obtained from a separate auto-fluorescence-only sample.

By way of comparison, the same image cube was analyzed in the same manner, where an adjacent tissue section was used as an autofluorescence "blank" sample to estimate the pure autofluorescence spectrum. The results are shown in FIG. 7B, with the autofluorescence spectrum shown as curve 76. A dye-bearing region in the image cube was selected, whose spectrum is shown as curve 75. The Nuance® software's "Manual Compute Spectra" function was used to compute the pure spectrum, which is shown as curve 77 in FIG. 7B.

The spectrum 77 is unlikely to be an accurate estimate of the actual Alexa® 488 spectrum. For example, it shows a strong response in the Texas Red band, which corresponds to excitation at wavelengths above 540 nm and emissions at wavelengths of 600 nm and more. Fluorescence with these characteristics is not expected for this dye.

In contrast, the spectrum 73 is consistent with expectations for this dye, except for the slight negative-going values below 480 nm in the DAPI band; the resulting spectrum 74, in which the dark band is set to zero, is consistent with known dye properties and has performed well in spectral unmixing experiments.

In some embodiments, the spectral estimate for the fluorescent dye that is determined can optionally be used to construct a spectral library in step 122 of FIG. 1. Other spectra can be received (e.g., measured, obtained from an accessible storage unit or location, or input by a user, for example) in optional step 121 and also used to construct the spectral library. In general, constructing the spectral library involves storing the spectral information (e.g., the pure spectra) in a format for later retrieval and use. Not all of the spectra received in step 121 need to have been obtained using the methods and systems disclosed herein. For example, they may have come from other measurements performed using the same instrument, or from synthetic predictions about expected response based on the properties of a given dye and the instrument, or from tabulated values obtained for similar equipment.

In optional step 131, the spectral library—including the pure spectrum of the dye that was determined—can be used to unmix multispectral images. Typically, the multispectral images that are unmixed in step 131 will be images of a second sample, different from the one used to calculate the pure dye spectrum. In other words, the methods and systems disclosed herein can be used to obtain pure spectrum estimates for dyes and other fluorescing entities in situ, and then use those estimates to quantitatively analyze multispectral images of other samples (e.g., other tissue sections and/or cell samples) The analysis of a second sample typically involves using the pure spectrum of the dye to determine, at each of multiple locations in the second sample, quantities of various fluorescent (and non-fluorescent) reporters as a function of spatial location in the sample. Methods for performing such analysis are disclosed, for example, in U.S. Pat. Nos. 8,391,961, 8,634,607, and 8,462,981. The process then ends at step 141.

ADDITIONAL EXAMPLES

The examples in this section, like those in the prior sections, are not intended to limit the scope of the claims, but only to further describe certain features of the subject matter disclosed herein.

Example 1

In this example, the sample was a breast cancer sample obtained as a formalin-fixed, paraffin-embedded (FFPE) tissue block, from which a 4 micron section was cut with a microtome, and then subjected to standard histology processes for dewaxing, antigen retrieval, and immuno-fluorescent (IF) labeling using a PR probe conjugated to Alexa® 594 dye (obtained from Life Sciences Solutions, Carlsbad, Calif.). It was counterstained with DAPI and then mounted on a standard microscope slide with a cover slip. It was imaged as discussed previously, using the same instrument, epi-filters and wavelengths.

Figure 8A:
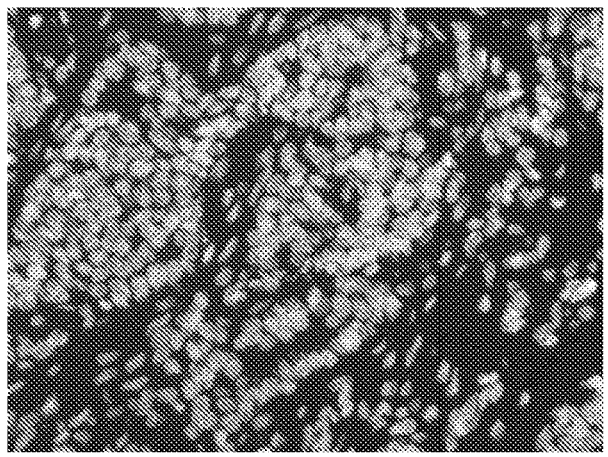
FIGS. 8A-8C are images showing the blue, green, and red planes, respectively, of a color rendering of an image cube with 23 layers corresponding to a multispectral image of a second breast cancer sample, prepared with a probe that targets progesterone receptor (PR), with a DAPI counterstain applied as well.
Figure 8B:
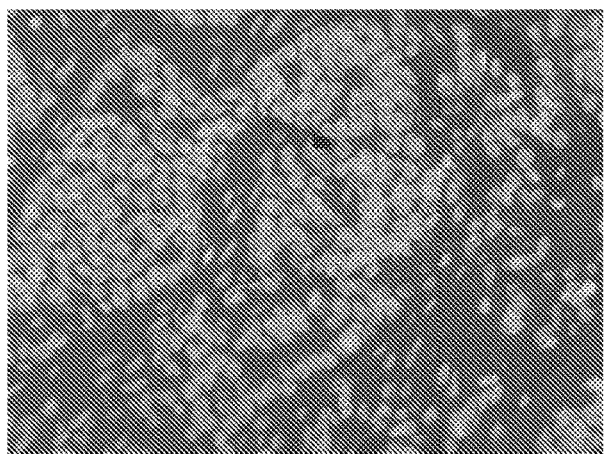
Figure 8C:
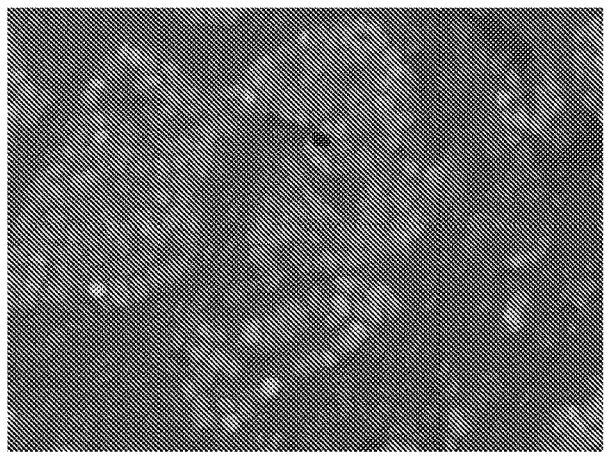

In this example, the goal was to determine the pure dye spectrum for Alexa® 594, so the dark band consisted of all image cube planes that were acquired with either the DAPI or FITC epi-filter, and the light band consisted of all image cube planes acquired with the Texas Red filter. A color image was produced of the image cube; the blue, green, and red color planes are shown as FIGS. 8A-8C, respectively.

Figure 9A:
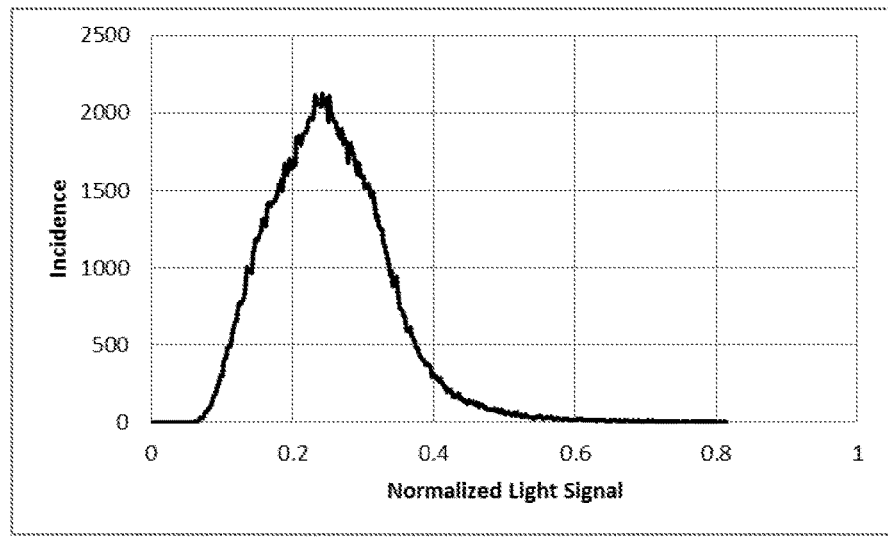
FIG. 9A is a plot showing a histogram of pixels in non-blank regions of the images in FIGS. 8A-8C, ranked by normalized signal strength in the dye-expression band.
Figure 9B:
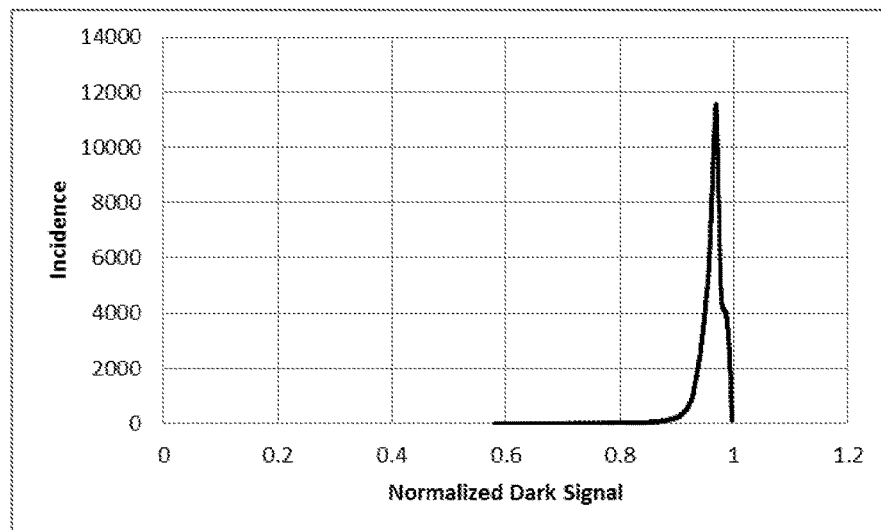
FIG. 9B is a plot showing a histogram of the same pixels as in FIG. 9A, ranked by normalized signal strength in the dark band.

Blank regions were identified in the same way, using a threshold of 2129 counts in $|S_{dark}|$, to choose sample-bearing regions. The histogram of $|S_{light}|$ shown in FIG. 9A was used to choose dye-enriched pixels, based on the 98% population signal strength percentile. These pixels were removed from the set of sample-bearing pixels to form a pixel set that contained sample and was not deemed to be dye-enriched; the histogram of $|S_{dark}|$ for these pixels shown in FIG. 9B was used to select dye-deficit pixels based on the 80% population signal strength criterion.

Figure 10A:
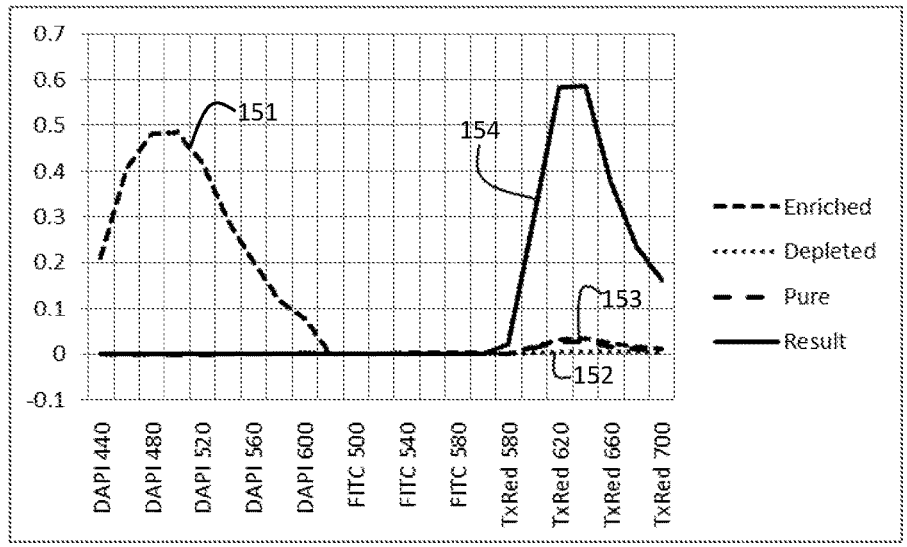
FIG. 10A is a plot showing the normalized spectra for preferentially dye-enriched pixels, dye-deficit pixels, the spectrum that was determined for the fluorescent dye, and the dye spectrum after setting the dark band elements to zero and normalizing to unit length, for the sample of FIGS. 8A-8C.

One thousand pixels were randomly selected from each of the pixel sets (dye-enriched and dye-deficit), and the mean spectra were calculated for each group. The pure dye spectrum was estimated using Equation (8), where λ was calculated using Equation (9) to produce a mean value of zero in the dark bands. The results are shown in FIG. 10A, where curve 151 shows the mean dye-enriched spectrum, curve 152 shows the mean dye-deficit spectrum, and curve 153 shows the pure dye spectrum before the dark-band signals were forced to zero. The normalized spectrum with dark bands set to zero is shown as curve 154.

Figure 10B:
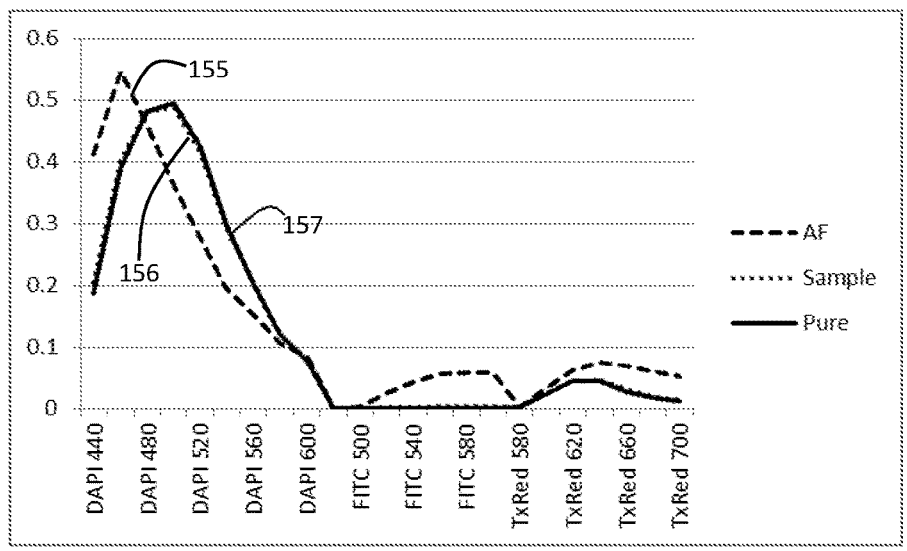
FIG. 10B is a plot showing the spectrum for the fluorescent dye and the mixed (dye and autofluorescence) spectrum for the sample of FIGS. 8A-8C, and the pure autofluorescence spectrum obtained from a separate auto-fluorescence-only sample.

For comparison purposes, a spectrum was calculated using the Nuance® software based on the same Alexa® 594 sample, and the autofluorescence witness sample discussed previously. The results are shown in FIG. 10B. A dye-bearing region was chosen from the Alexa® 594 sample whose spectrum is shown by curve 155, and selected autofluorescence regions from the witness sample whose spectrum is shown by curve 156. The "Manual Compute Spectrum" function of Nuance® was used to produce a pure-dye spectrum shown by curve 157 in FIG. 10B.

Example 2

Figure 11A:
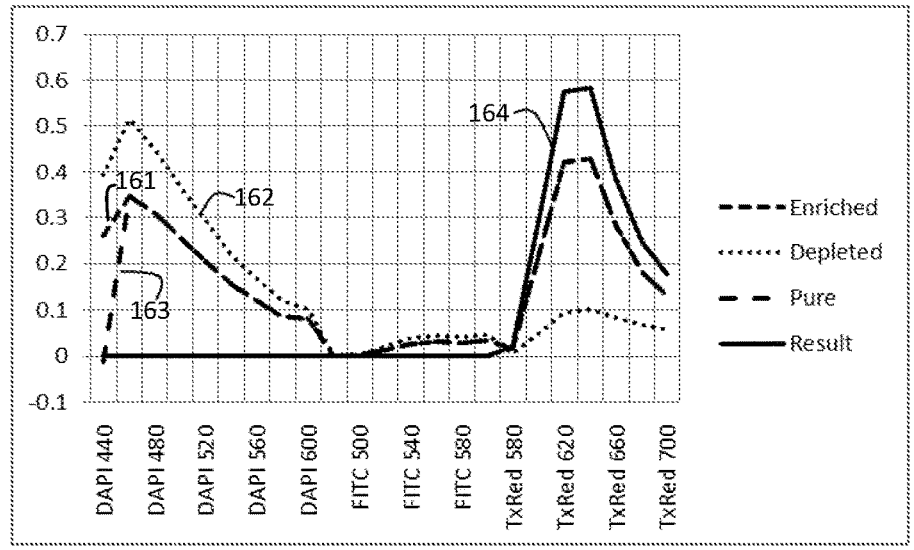
FIG. 11A is a plot showing the normalized spectra for preferentially dye-enriched pixels and dye-deficit pixels, the spectrum that was determined for a breast cancer tissue sample containing the fluorescent dye, and the dye spectrum after setting the dark band elements to zero and normalizing to unit length.

The same procedure as in Example 1 was followed on another sample from the same tissue block, to which no DAPI counterstain was applied. FIG. 11A shows the obtained mean dye-enriched, dye-deficit, and pure dye spectra as curves 161, 162, and 163, respectively. The dark bands were then set to zero and the resulting spectrum was normalized; the result is shown as curve 164.

Figure 11B:
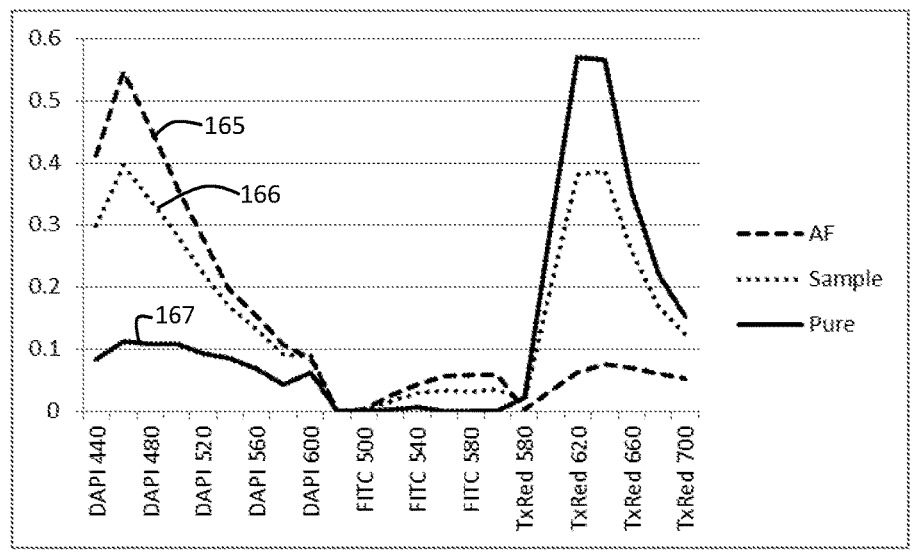
FIG. 11B is a plot showing the calculated spectrum for the fluorescent dye and the mixed (dye and autofluorescence) spectrum for the sample of FIGS. 8A-8C, and the pure autofluorescence spectrum obtained from a separate auto-fluorescence-only sample.

Nuance® was used to measure the spectrum based on this sample for the Alexa® 594 dye, with the same autofluorescence blank as in the previous examples. The same operator performed the same steps as described previously; the dye-bearing, auto-fluorescent, and pure spectra that were obtained are shown in FIG. 11B as curves 165, 166, and 167, respectively.

Comparing curve 154 and 164, there is not a great difference between them, indicating that a good estimate of the Alexa® 594 signal was obtained despite the presence of a strong, confounding DAPI signal that localizes in the nucleus—the same cell compartment in which the PR antibody, and hence the Alexa® 594, were primarily localized.

In contrast, curves 157 and 167 are markedly different. These were determined using a method that relied on an autofluorescence "blank" spectrum 156 to purify the mixed signal 155. That gave poor results when the dye-bearing sample had a different background signal, due to the presence of the confounding DAPI emissions. Even spectrum 167 has strong response to the DAPI epi-filter, which is unlikely to be accurate given the known properties of this dye.

Example 3

In a further example, the sample was a breast cancer sample obtained as a formalin-fixed, paraffin-embedded (FFPE) tissue block, from which a 4 micron section was cut with a microtome, and then subjected to standard histology processes for dewaxing and antigen retrieval. However, no immuno-fluorescent (IF) labeling was performed. It was counterstained with DAPI and then mounted on a standard microscope slide with a cover slip. It was imaged as in the previous example, using the same instrument, epi-filters and wavelengths as described there.

The pure DAPI spectrum was determined according to the methods disclosed herein, using all image cube layers for which the FITC epi-filter was engaged as the dark band. The light band consisted of all image cube layers for which the DAPI epi-filter was engaged. Image cube layers acquired with the Texas Red epi-filter was engaged were not assigned to either the dark band or the light band. The same procedure and thresholds were used as in the previous examples to choose dye-enriched and dye-deficit pixels.

Figure 12A:
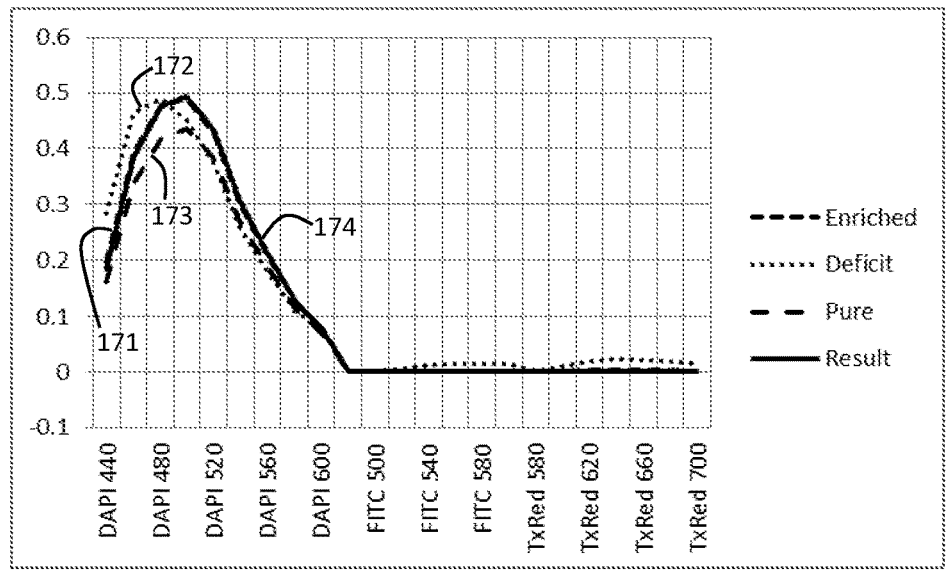
FIG. 12A is a plot showing the normalized spectra for preferentially dye-enriched pixels, dye-deficit pixels, the spectrum that was determined for a breast cancer tissue sample counterstained with DAPI, and the DAPI spectrum after setting the dark band elements to zero and normalizing to unit length.
Figure 12B:
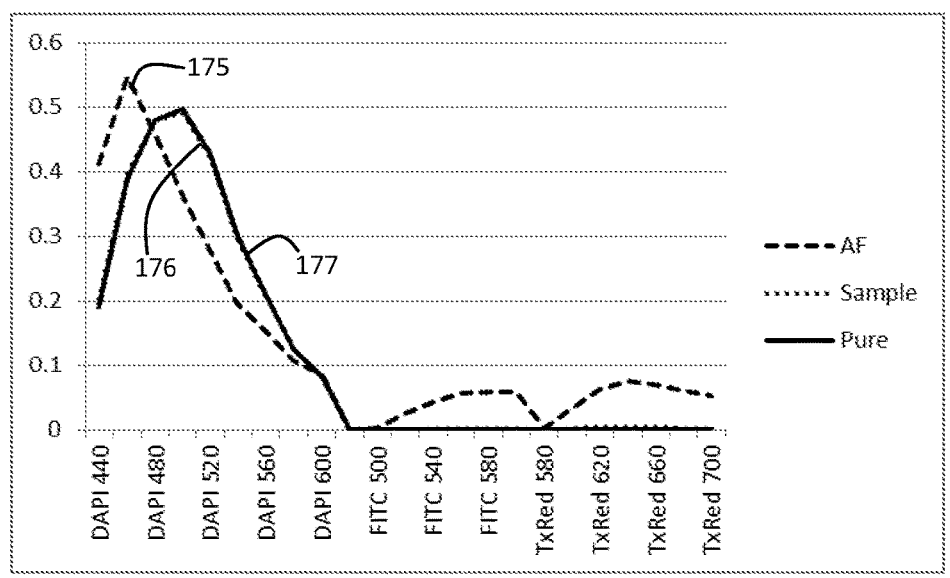
FIG. 12B is a plot showing the calculated spectrum for DAPI in the sample of FIG. 12A, the mixed (dye and autofluorescence) spectrum from the sample, and the pure autofluorescence spectrum obtained from a separate auto-fluorescence-only sample.

The mean spectra for the dye-enriched and dye-deficit pixel sets are shown in FIG. 12A as curves 171 and 172. Curve 173 depicts the pure spectrum obtained using Equation (8) where 2 was chosen using Equation (9). In this example, the signal in the dark band was set to zero, and the signal in all other bands was clipped to prevent negative-going values, and then normalized to unit length. The result is shown as curve 124 in FIG. 12A. Autofluorescence (curve 175), sample (curve 176), and pure (curve 177) spectra obtained with the Nuance® software in the manner described above in connection with previous examples are shown in FIG. 12B.

Example 4

In another example, a multiplexed sample was produced from a breast cancer tissue sample obtained as a formalin-fixed, paraffin-embedded (FFPE) tissue block, from which a 4 micron section was cut with a microtome, and then subjected to standard histology processes for dewaxing, antigen retrieval, and immuno-fluorescent (IF) labeling using a PR probe conjugated to Alexa® 594 dye along with an ER probe conjugated to Alexa® 488 dye. It was counterstained with DAPI at a dilution of 1:20,000 and then mounted on a standard microscope slide with a cover slip.

Figure 13A:
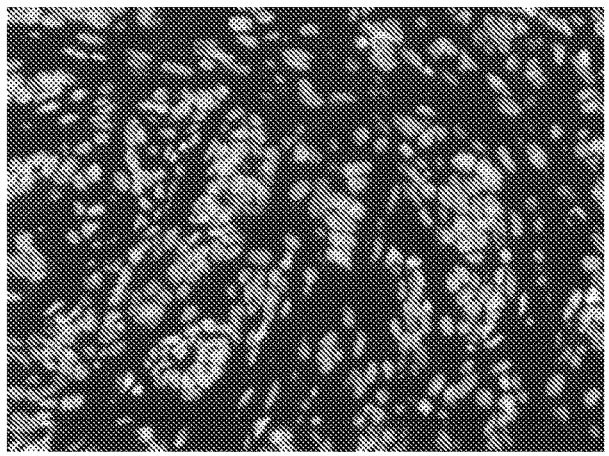
FIGS. 13A-13C are images that show the blue, green and red planes of a color rendering of an image cube acquired of a multiplexed breast cancer sample, prepared with a DAPI counterstain, an ER probe bound to Alexa® 488 fluorescent dye, and a PR probe bound to Alexa® 594 fluorescent dye.
Figure 13B:
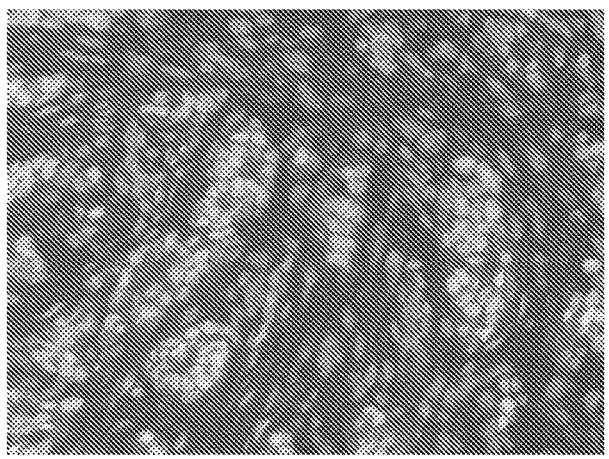
Figure 13C:
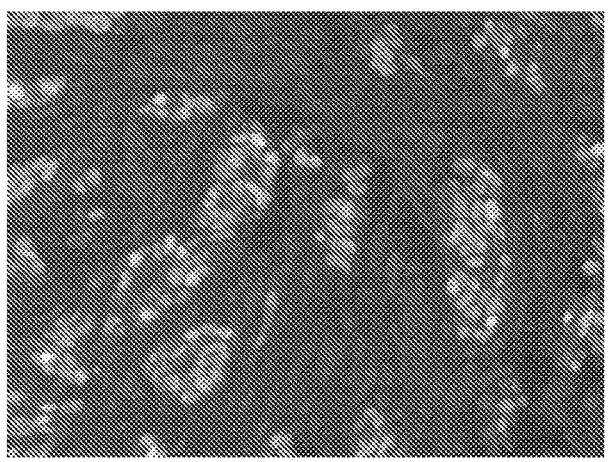

An autofluorescence blank was produced from an adjacent section cut from the same block, then subjected to the same histology procedures excepting that neither probes nor counterstain was applied. The sample and the autofluorescence blank were imaged using the same Vectra® system described previously, using the same epi-filters and wavelengths. The blue, green, and red planes of a color rendering of the image cube are shown in FIGS. 13A-13C, respectively.

A tissue-bearing region of the autofluorescence blank was chosen, and the mean spectrum was obtained for those pixels. A spectral library was assembled from this autofluorescence spectrum and the Alexa® 488, Alexa® 594, and DAPI spectra determined from the other examples described above.

Figure 14A:
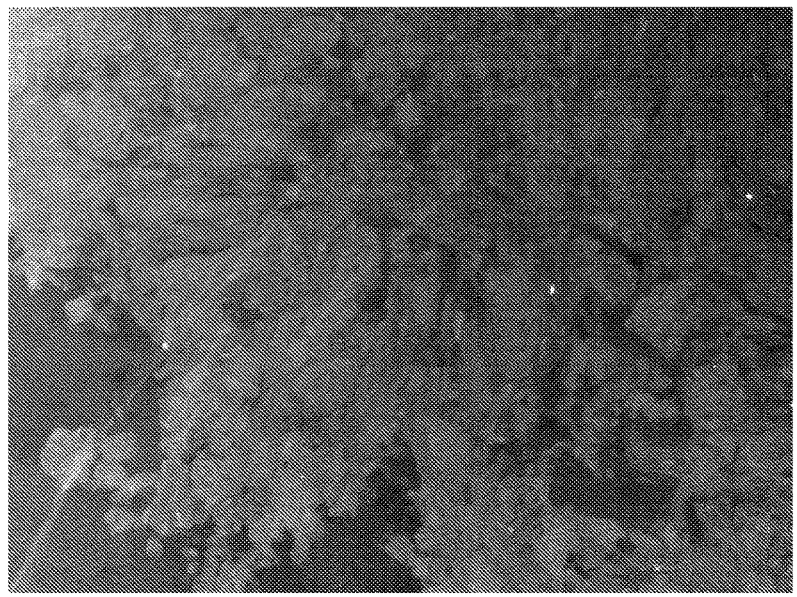
FIGS. 14A-14D are unmixed component images for the sample of FIGS. 13A-13C when unmixed with a spectral library containing autofluorescence, DAPI, Alexa® 488, and Alexa® 594, respectively.
Figure 14B:
Figure 14C:
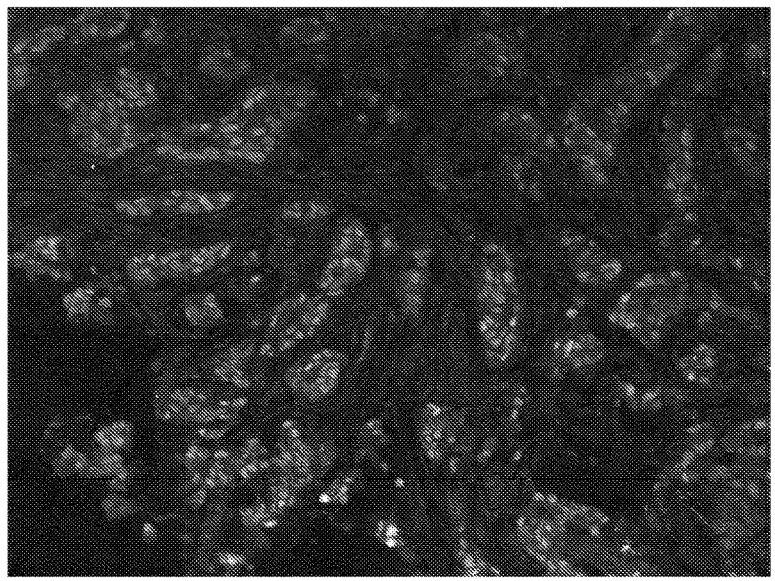
Figure 14D:
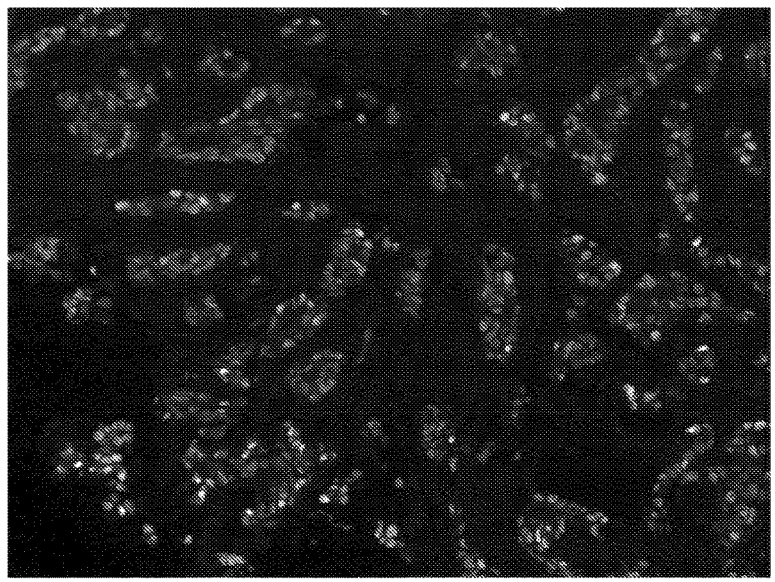

The multiplexed sample image cube was unmixed using this library, and component images were generated that represented the distribution of each dye, and of autofluorescence, in the sample. These are shown as FIG. 14A (unmixed autofluorescence image), FIG. 14B (unmixed Alexa® 488 image), FIG. 14C (unmixed Alexa® 594 image), and FIG. 14D (unmixed DAPI image).

Image Analysis and Object Classification

The result of spectral unmixing is a set of component images that indicate the location and amount of the various stains and other sample components. The component images are a rich dataset for various kinds of image analysis, including expression measurements, co-localization, positivity analysis, and assessment of biomarker indices (cancer prognostics, patient stratification, etc.) that involve these quantities, or any quantitative measurement of stained tissue.

The component images are suitable for image analysis and object classification using the techniques described, for example, in U.S. Pat. No. 7,155,555 and U.S. Pat. No. 8,280,140, the entire contents of each of which are incorporated herein by reference. Thus the systems and methods disclosed herein can provide for acquiring images and processing them as described above, image pre-processing and unmixing into component images, object classification to find tissue structures, cells, or sub-cellular compartments, and measurement of protein expression by assessing signal levels in the unmixed components.

It was noted above that the determination of what regions are sample-bearing and which are empty is rarely if ever perfect. In the present examples, choosing a more stringent criterion for sample being present was not disadvantageous. This is because if one excludes a small percentage of pixels that actually contain sample, it does not strongly affect the selection of either the dye-enriched pixel set, or the dye-deficient pixel set. The former is true because in the samples used here, the dye tends to localize in cellular compartments for which there is significant autofluorescence. Thus using a somewhat higher histogram cutoff for dark-band signal strength $|S_{dark}|$ is not likely to reject dye-enriched pixels. Instead, it rejects fainter autofluorescent structures such as stroma. Nor is it likely to reject most dye-deficient pixels, since these pixels are chosen based on the relative proportion of the dark band signal in their overall signal.

The improved accuracy provided by the systems and methods disclosed herein results in more accurate measurements of samples that contain multiple dyes. It also means that spatially co-localized fluorescent probes can be detected or measured more reliably.

Multispectral Imaging Systems

Figure 15:
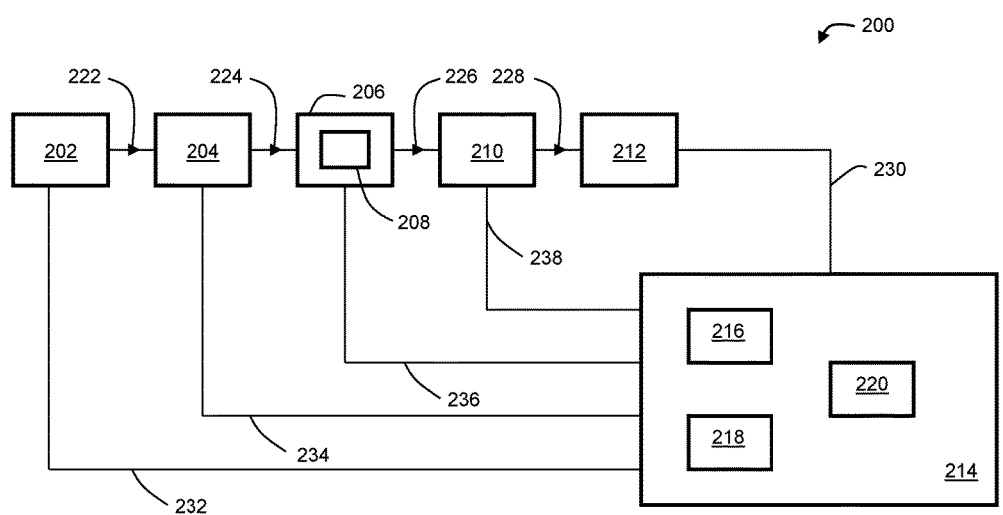
FIG. 15 is a schematic diagram of a multispectral imaging system.

FIG. 15 is a schematic diagram showing a system 200 for acquiring multiple spectrally resolved images of a sample. System 200 can be used to acquire multispectral images (e.g., image cubes), and also to analyze the multispectral image information (e.g., by performing any of the steps disclosed herein).

A light source 202 provides light 222 to light conditioning optics 204. Light 222 can be incoherent light, such as light generated from a filament source for example, or light 222 can be coherent light, such as light generated by a laser. Light 222 can be either continuous-wave (CW) or time-gated (i.e., pulsed) light. Further, light 222 can be provided in a selected portion of the electromagnetic spectrum. For example, light 222 can have a central wavelength and/or a distribution of wavelengths that falls within the ultraviolet, visible, infrared, or other regions of the spectrum.

Light conditioning optics 204 can be configured to transform light 222 in a number of ways. For example, light conditioning optics 204 can spectrally filter light 222 to provide output light in a selected wavelength region of the spectrum. Alternatively, or in addition, light conditioning optics can adjust the spatial distribution of light 222 and the temporal properties of light 222. Incident light 224 is generated from light 222 by the action of the elements of light conditioning optics 204.

Incident light 224 is directed to be incident on sample 208 mounted on illumination stage 206. Stage 206 can provide means to secure sample 208, such as mounting clips or other fastening devices. Alternatively, stage 206 can include a movable track or belt on which a plurality of samples 208 are affixed. A driver mechanism can be configured to move the track in order to successively translate the plurality of samples, one at a time, through an illumination region on stage 206, whereon incident light 224 impinges. Stage 206 can further include translation axes and mechanisms for translating sample 208 relative to a fixed position of illumination stage 206. The translation mechanisms can be manually operated (e.g., threaded rods) or can be automatically movable via electrical actuation (e.g., motorized drivers, piezoelectric actuators).

In response to incident light 224, emitted light 226 emerges from sample 208. Emitted light 226 can be generated in a number of ways. For example, in some embodiments, emitted light 226 corresponds to a portion of incident light 224 transmitted through sample 208. In other embodiments, emitted light 226 corresponds to a portion of incident light 224 reflected from sample 208. In yet further embodiments, incident light 224 can be absorbed by sample 208, and emitted light 226 corresponds to fluorescence emission from sample 208 (e.g., from fluorescent components in sample 208) in response to incident light 224. In still further embodiments, sample 208 can be luminescent, and may produce emitted light 226 even in the absence of incident light 224. In some embodiments, emitted light 226 can include light produced via two or more of the foregoing mechanisms.

In many embodiments, sample 208 is a biological sample such as a tissue slice (e.g., a sample used for pathology, or a cell suspension or smear, as in cytology studies), or living or fixed cells in tissue culture.

Light collecting optics 210 are positioned to received emitted light 226 from sample 208. Light collecting optics 210 can be configured to collimate emitted light 226 when light 226 is divergent, for example. Light collecting optics 210 can also be configured to spectrally filter emitted light 226. Filtering operations can be useful, for example, in order to isolate a portion of emitted light 226 arising via one of the mechanisms discussed above from light arising via other processes. For example, the methods described herein are used to determine accurate estimates of the fluorescence spectra of one or more dyes in a sample. Light collecting optics 210 can be configured to filter out non-fluorescence components of emitted light 226 (e.g., components corresponding to transmitted and/or reflected incident light). Further, light collecting optics 210 can be configured to modify the spatial and/or temporal properties of emitted light 226 for particular purposes in embodiments. Light collecting optics 210 transform emitted light 226 into output light 228 which is incident on detector 212.

Detector 212 includes one or more elements such as CCD sensors configured to detect output light 228. In some embodiments, detector 212 can be configured to measure the spatial and/or temporal and/or spectral properties of light 228. Detector 212 generates an electrical signal that corresponds to output light 228, and is communicated via electrical communication line 230 to electronic control system 214.

Electronic control system 214 includes a processor 216, a display device 218, and a user interface 220. In addition to receiving signals corresponding to output light 228 detected by detector 212, control system 214 sends electrical signals to detector 212 to adjust various properties of detector 212. For example, if detector 212 includes a CCD sensor, control system 214 can send electrical signals to detector 212 to control the exposure time, active area, gain settings, and other properties of the CCD sensor.

Electronic control system 214 also communicates with light source 202, light conditioning optics 204, illumination stage 206, and light collecting optics 210 via electrical communication lines 232, 234, 236, and 238, respectively. Control system 214 provides electrical signals to each of these elements of system 200 to adjust various properties of the elements. For example, electrical signals provided to light source 202 can be used to adjust the intensity, wavelength, repetition rate, or other properties of light 222. Signals provided to light conditioning optics 204 and light collecting optics 210 can include signals for configuring properties of devices that adjust the spatial properties of light (e.g., spatial light modulators) and for configuring spectral filtering devices, for example. Signals provided to illumination stage 206 can provide for positioning of sample 208 relative to stage 206 and/or for moving samples into position for illumination on stage 206, for example.

Control system 214 includes a user interface 220 for displaying system properties and parameters, and for displaying captured images of sample 208. User interface 220 is provided in order to facilitate operator interaction with, and control over, system 200. Processor 216 includes a storage device for storing image data captured using detector 212, and also includes computer software that embodies instructions to processor 216 that cause processor 216 to carry out control functions, such as those discussed above for example. Further, the software instructions cause processor 216 to mathematically manipulate the images captured by detector 212 and to carry out the steps of classifying sample 208 according to either or both of the original and the manipulated images. The classification steps are described in more detail subsequently.

In some embodiments, light conditioning optics 204 include an adjustable spectral filter element such as a filter wheel or a liquid crystal spectral filter. The filter element can be configured to provide for illumination of sample 108 using different light wavelength bands. Light source 202 can provide light 222 having a broad distribution of spectral wavelength components. A selected region of this broad wavelength distribution is allowed to pass as incident light 224 by the filter element in light conditioning optics 204, and directed to be incident on sample 208. Subsequently, the wavelength of the filter pass-band in light conditioning optics 204 is changed to provide incident light 224 having a different wavelength. Spectrally-resolved images can also be recorded by employing a light source 202 having multiple source elements generating light of different wavelengths, and alternately turning the different source elements on and off to provide incident light 224 having different wavelengths.

Light collecting optics 210 can include configurable spectral filter elements similar to those discussed above in connection with light conditioning optics 204. Therefore, spectral resolution can be provided on the excitation side of sample 208 (e.g., via light conditioning optics 204) and on the emission side of sample 208 (e.g., via light collecting optics 210).

The result of collecting multiple, spectrally resolved images of sample 208 is an "image stack" where each image in the stack is a two-dimensional image of the sample corresponding to a particular wavelength. Conceptually, the set of images can be visualized as forming a three-dimensional matrix, where two of the matrix dimensions are the spatial length and width of each of the images, and the third matrix dimension is the spectral index. For this reason, the set of spectrally resolved images can be referred to as a "spectral cube" of images. As used herein, a "pixel" in such a set of images (or image stack or spectral cube), refers to a common spatial location for each of the images. Accordingly, a pixel in a set of images includes a value associated with each image at the spatial location corresponding to the pixel.

Hardware and Software Implementation

Figure 16:
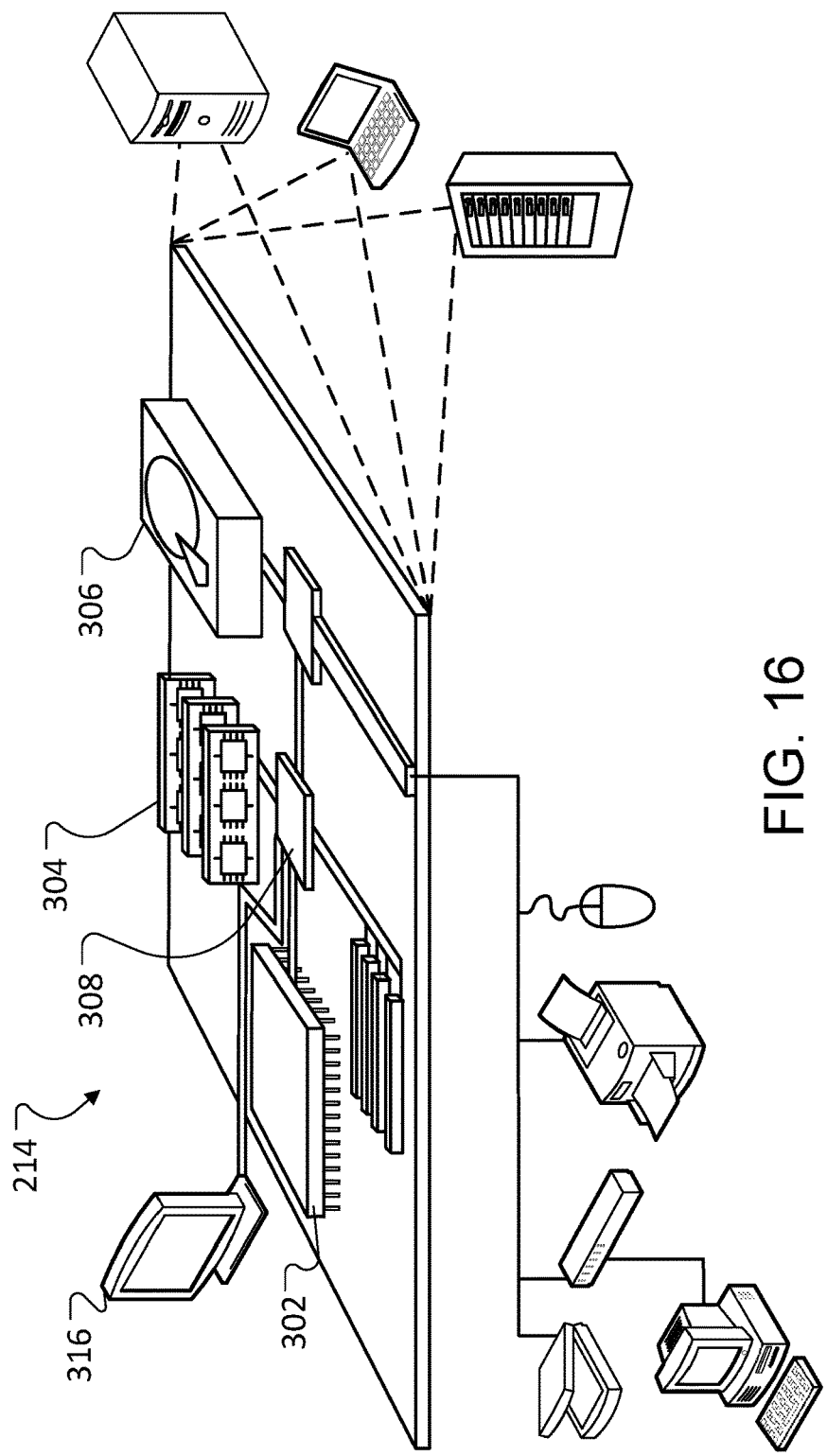
FIG. 16 is a schematic diagram of an electronic control system.

FIG. 16 shows an example of an electronic control system 214, which may be used with the systems and methods disclosed herein. Electronic control system can include one or more processors 302 (e.g., corresponding to processor 216 in FIG. 15), memory 304, a storage device 306 and interfaces 308 for interconnection. The processor 302 can process instructions for execution within the electronic control system 214, including instructions stored in the memory 304 or on the storage device 306. For example, the instructions can instruct the processor 302 to perform any of the analysis and control steps disclosed herein.

The memory 304 can store executable instructions for processor 302, information about parameters of the system such as excitation and detection wavelengths, and measured spectral image information. The storage device 306 can be a computer-readable medium, such as a floppy disk device, a hard disk device, an optical disk device, or a tape device, a flash memory or other similar solid state memory device, or an array of devices, including devices in a storage area network or other configurations. The storage device 306 can store instructions that can be executed by processor 302 described above, and any of the other information that can be stored by memory 304.

In some embodiments, electronic control system 214 can include a graphics processing unit to display graphical information (e.g., using a GUI or text interface) on an external input/output device, such as display 316. The graphical information can be displayed by a display device (e.g., a CRT (cathode ray tube) or LCD (liquid crystal display) monitor) for displaying any of the information, such as measured and calculated spectra and images, disclosed herein. A user can use input devices (e.g., keyboard, pointing device, touch screen, speech recognition device) to provide input to the electronic control system 214.

The methods disclosed herein can be implemented by electronic control system 214 (and processors 302 and 216) by executing instructions in one or more computer programs that are executable and/or interpretable on the electronic control system 214. These computer programs (also known as programs, software, software applications or code) include machine instructions for a programmable processor, and can be implemented in a high-level procedural and/or object-oriented programming language, and/or in assembly/machine language. For example, computer programs can contain the instructions that can be stored in memory 304, in storage unit 306, and/or on a computer-readable medium, and executed by processor 302 (processor 216) as described above. As used herein, the term "computer-readable medium" refers to any computer program product, apparatus and/or device (e.g., magnetic discs, optical disks, memory, Programmable Logic Devices (PLDs), ASICs, and electronic circuitry) used to provide machine instructions and/or data to a programmable processor, including a machine-readable medium that receives machine instructions.

Generally, electronic control system 214 can be implemented in a computing system to implement the operations described above. For example, the computing system can include a back end component (e.g., as a data server), or a middleware component (e.g., an application server), or a front end component (e.g., a client computer having a graphical user-interface), or any combination thereof.

OTHER EMBODIMENTS

While this disclosure describes specific implementations, these should not be construed as limitations on the scope of the disclosure, but rather as descriptions of features in certain embodiments. Features that are described in the context of separate embodiments can also generally be implemented in combination in a single embodiment. Conversely, various features that are described in the context of a single embodiment can also be implemented in multiple embodiments separately or in any suitable sub-combination. Moreover, although features may be described above as present in certain combinations and even initially claimed as such, one or more features from a claimed combination can generally be excised from the combination, and the claimed combination may be directed to a sub-combination or variation of a sub-combination.

In addition to the embodiments expressly disclosed herein, it will be understood that various modifications to the embodiments described may be made without departing from the spirit and scope of the disclosure. Accordingly, other embodiments are within the scope of the following claims.

What is claimed is:

1. A method, comprising:
obtaining multispectral image information for a sample comprising a fluorescent dye, wherein the multispectral image information forms an image cube comprising multiple two-dimensional layers, each layer comprising an image of the sample;
calculating from the image cube a first spectrum comprising contributions from endogenous fluorescence in the sample;
calculating from the image cube a second spectrum comprising contributions from the fluorescent dye and from endogenous fluorescence in the sample; and
calculating a pure spectrum of the fluorescent dye in the sample based on the first and second spectra,
wherein a relative contribution of light emission from the fluorescent dye to the second spectrum is larger than a relative contribution of light emission from the fluorescent dye to the first spectrum;
wherein calculating the first spectrum comprises identifying a first set of pixel intensity values in the image cube corresponding to a first set of pixel locations, and using the first set of pixel intensity values to calculate the first spectrum;
wherein calculating the second spectrum comprises identifying a second set of pixel intensity values in the image cube corresponding to a second set of pixel locations, the second set of pixel locations being different from the first set of pixel locations, and using the second set of pixel intensity values to calculate the second spectrum; and
wherein identifying the first set of pixel intensity values comprises designating one or more layers of the image cube as a first layer set, and identifying members of the first set of pixel intensity values based on the first layer set.

2. The method of claim 1, wherein the first spectrum comprises contributions from the fluorescent dye.

3. The method of claim 1, wherein relative contributions from light emission by other components in the sample are reduced in the pure spectrum of the fluorescent dye relative to the second spectrum.

4. The method of claim 2, wherein relative contributions from light emission by other components in the sample are minimized in the pure spectrum of the fluorescent dye relative to the second spectrum.

5. The method of claim 1, further comprising, for each candidate pixel in the first layer set, determining whether the pixel is a member of the first set of pixel intensity values based on a fraction of total pixel intensity that is attributable to the first layer set.

6. The method of claim 1, further comprising designating one or more layers of the image cube as a second layer set, and identifying members of the second set of pixel intensity values based on the second layer set.

7. The method of claim 6, further comprising, for each candidate pixel in the first layer set, determining whether the pixel is a member of the first set of pixel intensity values based on a fraction of total pixel intensity that is attributable to the first layer set.

8. The method of claim 7, further comprising, for each candidate pixel in the second layer set, determining whether the pixel is a member of the second set of pixel intensity values based on a fraction of total pixel intensity that is attributable to the second layer set.

9. The method of claim 1, further comprising identifying pixels that correspond to a portion of the sample based on the first set of layers.

10. The method of claim 1, further comprising:
adding the pure spectrum of the fluorescent dye to a spectral library;
obtaining a second set of multispectral image information for a second sample corresponding to a second image cube, wherein the second sample comprises the fluorescent dye; and
using the spectral library to unmix the second image cube to determine an amount of the fluorescent dye at multiple spatial locations in the second sample.

11. The method of claim 10, wherein the second sample comprises a fluorescent counterstain, the method further comprising determining relative amounts of the fluorescent dye and the fluorescent counterstain at the multiple spatial locations in the second sample.

12. The method of claim 1, further comprising determining the pure spectrum by subtracting from the second spectrum a scaled multiple of the first spectrum.

13. The method of claim 12, further comprising determining a value of a scaling coefficient that multiplies the first spectrum from pixel intensity values that correspond to multiple pixels in the image cube.

14. A system, comprising:
a radiation source configured to direct illumination radiation to a sample comprising a fluorescent dye;
a detector configured to obtain images of the sample by detecting light emitted from the sample; and
an electronic processor and stored instructions configured to:
obtain multispectral image information for the sample from one or more images obtained by the detector, the multispectral image information forming an image cube comprising multiple two-dimensional layers, each layer comprising an image of the sample;
calculate from the image cube a first spectrum comprising contributions from endogenous fluorescence in the sample;
calculate from the image cube a second spectrum comprising contributions from the fluorescent dye and from endogenous fluorescence in the sample; and
calculate a pure spectrum of the fluorescent dye in the sample based on the first and second spectra,
wherein a relative contribution of light emission from the fluorescent dye to the second spectrum is larger than a relative contribution of light emission from the fluorescent dye to the first spectrum;
wherein calculating the first spectrum comprises identifying a first set of pixel intensity values in the image cube corresponding to a first set of pixel locations, and using the first set of pixel intensity values to calculate the first spectrum;
wherein calculating the second spectrum comprises identifying a second set of pixel intensity values in the image cube corresponding to a second set of pixel locations, the second set of pixel locations being different from the first set of pixel locations, and using the second set of pixel intensity values to calculate the second spectrum; and
wherein identifying the first set of pixel intensity values comprises designating one or more layers of the image cube as a first layer set, and identifying members of the first set of pixel intensity values based on the first layer set.

15. The system of claim 14, wherein the first spectrum comprises contributions from the fluorescent dye.

16. The system of claim 14, wherein relative contributions from light emission by other components in the sample are reduced in the pure spectrum of the fluorescent dye relative to the second spectrum.

17. The system of claim 16, wherein relative contributions from light emission by other components in the sample are minimized in the pure spectrum of the fluorescent dye relative to the second spectrum.

18. The system of claim 14, wherein the electronic processor is configured, for each candidate pixel in the first layer set, to determine whether the pixel is a member of the first set of pixel intensity values based on a fraction of total pixel intensity that is attributable to the first layer set.

19. The system of claim 14, wherein the electronic processor is configured to designate one or more layers of the image cube as a second layer set, and to identify members of the second set of pixel intensity values based on the second layer set.

20. The system of claim 19, wherein the electronic processor is configured, for each candidate pixel in the first layer yet, to determine whether the pixel is a member of the first set of pixel intensity values based on a fraction of total pixel intensity that is attributable to the first layer set.

21. The system of claim 20, wherein the electronic processor is configured, for each candidate pixel in the second layer set, to determine whether the pixel is a member of the second set of pixel intensity values based on a fraction of total pixel intensity that is attributable to the second layer set.

22. The system of claim 14, wherein the electronic processor is configured to identify pixels that correspond to a portion of the sample based on the first set of layers.

23. The system of claim 14, wherein the electronic processor is configured to:
add the pure spectrum of the fluorescent dye to a spectral library;
obtain a second set of multispectral image information for a second sample corresponding to a second image cube from one or more images obtained by the detector, wherein the second sample comprises the fluorescent dye; and
use the spectral library to unmix the second image cube to determine an amount of the fluorescent dye at multiple spatial locations in the second sample.

24. The system of claim 23, wherein the second sample comprises a fluorescent counterstain, and wherein the electronic processor is configured to determine relative amounts of the fluorescent dye and the fluorescent counterstain at the multiple spatial locations in the second sample.

25. The system of claim 14, wherein the electronic processor is configured to determine the pure spectrum by subtracting from the second spectrum a scaled multiple of the first spectrum.

26. The method of claim 25, wherein the electronic processor is configured to determine a value of a scaling coefficient that multiplies the first spectrum from pixel intensity values that correspond to multiple pixels in the image cube.

27. A method, comprising:
- obtaining multispectral image information for a sample comprising a fluorescent dye, wherein the multispectral image information forms an image cube comprising multiple two-dimensional layers, each layer comprising an image of the sample;
- designating at least one layer of the image cube as a first layer set corresponding to a dark band of the fluorescent dye;
- determining a first spectrum and a second spectrum based on respective first and second sets of pixel intensity values from the image cube; and
- calculating a pure spectrum of the fluorescent dye in the sample based on the first and second spectra and the first layer set,
- wherein the first set of pixel intensity values corresponds to a first set of pixel locations in the image cube and the second set of pixel intensity values corresponds to a second set of pixel locations in the image cube, the first set of pixel locations being different from the second set of pixel locations; and
- wherein a relative contribution of light emission from the fluorescent dye to the pixel intensity values is larger for the second set of pixel intensity values than for the first set of pixel intensity values.

28. The method of claim 27, wherein calculating the pure spectrum comprises minimizing contributions from the pure spectrum in the first layer set.

29. The method of claim 27, further comprising determining the pure spectrum by subtracting from the second spectrum a scaled multiple of the first spectrum.

30. The method of claim 29, further comprising determining a value of a scaling coefficient that multiplies the first spectrum from pixel intensity values that correspond to multiple pixels in the image cube.

* * * * *

UNITED STATES PATENT AND TRADEMARK OFFICE
CERTIFICATE OF CORRECTION

PATENT NO. : 10,126,242 B2
APPLICATION NO. : 14/795430
DATED : November 13, 2018
INVENTOR(S) : Peter J. Miller and Kent S. Johnson It is certified that error appears in the above-identified patent and that said Letters Patent is hereby corrected as shown below:

In the Claims

Column 28
Line 65, in Claim 26, delete "method" and insert -- system --

Signed and Sealed this
Twenty-sixth Day of March, 2019

Andrei Iancu
*Director of the United States Patent and Trademark Office*